US012402799B2

(12) United States Patent
Doan et al.

(10) Patent No.: US 12,402,799 B2
(45) Date of Patent: Sep. 2, 2025

(54) WIRELESS MEMS LEFT ATRIAL PRESSURE SENSOR

(71) Applicant: Pacesetter, Inc., Sylmar, CA (US)

(72) Inventors: Phong D. Doan, San Clemente, CA (US); Apratim Dixit, Venice, CA (US)

(73) Assignee: Pacesetter, Inc., Sylmar (CA)

( * ) Notice: Subject to any disclaimer, the term of this patent is extended or adjusted under 35 U.S.C. 154(b) by 152 days.

(21) Appl. No.: 18/466,965

(22) Filed: Sep. 14, 2023

(65) Prior Publication Data
US 2023/0414118 A1   Dec. 28, 2023

Related U.S. Application Data

(60) Continuation of application No. 16/140,385, filed on Sep. 24, 2018, now Pat. No. 11,793,413, which is a division of application No. 13/767,398, filed on Feb. 14, 2013, now Pat. No. 10,130,268, which is a continuation of application No. 13/755,379, filed on Jan. 31, 2013, now Pat. No. 10,098,551.

(51) Int. Cl.
*A61B 5/0215* (2006.01)
*A61B 5/00* (2006.01)

(52) U.S. Cl.
CPC .......... *A61B 5/0215* (2013.01); *A61B 5/0004* (2013.01); *A61B 5/6852* (2013.01); *A61B 5/6869* (2013.01)

(58) Field of Classification Search
CPC ... A61B 5/0215; A61B 5/0004; A61B 5/6852; A61B 5/6869
See application file for complete search history.

(56) References Cited

U.S. PATENT DOCUMENTS

| | | | |
|---|---|---|---|
| 5,056,516 A | 10/1991 | Spehr | |
| 6,332,089 B1 * | 12/2001 | Acker | A61N 7/02 128/899 |
| 7,274,965 B1 | 9/2007 | Karicherla et al. | |
| 7,317,951 B2 | 1/2008 | Schneider et al. | |
| 7,515,971 B1 | 4/2009 | Doan | |
| 7,899,550 B1 | 3/2011 | Doan et al. | |
| 7,974,675 B2 | 7/2011 | Doan | |
| 7,976,551 B1 | 7/2011 | Gutfinger | |
| 8,267,863 B2 | 9/2012 | Najafi et al. | |
| 8,308,759 B2 | 11/2012 | Olsen | |
| 9,220,905 B2 | 12/2015 | Griswold et al. | |
| 2002/0077556 A1 | 6/2002 | Schwartz | |
| 2004/0073242 A1 | 4/2004 | Chanduszko | |
| 2004/0077988 A1 | 4/2004 | Tweden et al. | |
| 2004/0116992 A1 | 6/2004 | Wardle et al. | |
| 2005/0085843 A1 | 4/2005 | Opolski | |
| 2005/0125032 A1 | 6/2005 | Whisenant | |
| 2005/0136385 A1 | 6/2005 | Mann et al. | |
| 2006/0047205 A1 | 3/2006 | Ludomirsky et al. | |
| 2007/0032734 A1 | 2/2007 | Najafi | |
| 2007/0049984 A1 | 3/2007 | Osypka | |
| 2007/0073337 A1 | 3/2007 | Abbott et al. | |
| 2007/0179583 A1 | 8/2007 | Goetzinger et al. | |

(Continued)

*Primary Examiner* — Jacqueline Cheng
*Assistant Examiner* — Tho Q Tran
(74) *Attorney, Agent, or Firm* — Dean D. Small; The Small Patent Law Group, LLC.

(57) ABSTRACT

Systems for monitoring left atrial pressure using implantable cardiac monitoring devices and, more specifically, to a left atrial pressure sensor implanted through a septal wall are presented herein.

20 Claims, 35 Drawing Sheets

(56) References Cited

U.S. PATENT DOCUMENTS

| | | |
|---|---|---|
| 2008/0176271 A1 | 7/2008 | Silver |
| 2009/0005656 A1 | 1/2009 | Najafi et al. |
| 2012/0004647 A1 | 1/2012 | Cowley |
| 2012/0165827 A1 | 6/2012 | Khairkhahan |
| 2012/0209345 A1 | 8/2012 | Shkurovich |
| 2013/0079758 A1 | 3/2013 | Goode |
| 2013/0079870 A1 | 3/2013 | Roeder |
| 2016/0324443 A1* | 11/2016 | Rowland ............... A61B 5/036 |

* cited by examiner

WIRELESS MEMS LEFT ATRIAL PRESSURE SENSOR

CROSS REFERENCE TO RELATED APPLICATIONS

This application is a continuation application of U.S. patent application Ser. No. 16/140,385, which is a divisional application of U.S. patent application Ser. No. 13/767,398 (now issued as U.S. Pat. No. 10,130,268), which is a continuation of U.S. patent application Ser. No. 13/755,379 (now issued as U.S. Pat. No. 10,098,551), filed Jan. 31, 2013. The contents of the forgoing applications and patents are incorporated herein by reference.

FIELD OF THE INVENTION

Aspects of the present disclosure relate to systems and methods related to implantable cardiac monitoring devices and, more specifically, to a left atrial pressure sensor implanted through a septal wall.

BACKGROUND OF THE INVENTION

Monitoring the left atrial pressure (LAP) of heart failure patients is an effective method of assessing and managing a patient's heart failure progression. Timely interventions including medication taken as immediately as possible after an increase in LAP would more effectively treat a patient and reduce unnecessary hospitalization. To date, devices and approaches to monitor surrogates of LAP have encountered significant technical challenges.

Hemodynamic monitoring systems using other measurements as a surrogate for direct measurement of LAP have been tested in clinical trials with mixed results. Lead-based pressure sensors situated in the right ventricle outflow tract (RVOT) were relatively ineffective in managing heart failure and were additionally vulnerable to lead-related reliability issues. Wireless MEMS pressure sensors situated in the pulmonary artery are ill-suited for at least a subpopulation of patients presenting with heart failure. For example, the assessment of LAP using surrogate measurements within the pulmonary artery may not be suitable for patients suffering from pulmonary hypertension or other pulmonary conditions.

A silicone lead-based LAP sensor has been shown to be relatively effective at managing heart failure in initial feasibility studies. However, silicone-based leads used in other medical devices have exhibited a vulnerability to reliability-related performance degradation. In addition, obtaining LAP measurements using the silicone lead-based LAP sensor may present several challenges that may be exacerbated by the routing of the leads necessary for the operation of the pressure sensor. In particular, access to the left atrium of the heart must be provided in a safe manner and the pressure sensors need to be implanted in a manner that ensures accurate pressure measurements and that minimizes the risk of device-related complications such as thrombus formation.

A need exists for improved devices and techniques for measuring LAP safely and accurately. In addition, a need exists for improved devices and techniques for measuring LAP that reduce the need for invasive procedures to operate and maintain the LAP measurement device, and that reduce the need for intrusive associated elements such as device leads to power the device and/or to transmit a signal encoding the measured LAP. Such a device would facilitate the safe and accurate monitoring of LAP, thereby enhancing the timeliness and quality of the treatment of heart failure in variety of patient populations.

BRIEF SUMMARY OF THE INVENTION

This disclosure presents a novel concept of the wireless MEMS LAP sensor and tools used to safely place the wireless MEMS sensor in the left atrium. A wireless LAP sensor would eliminate negative perceptions associated with silicone bodied leads and device-pocket infections and would provide clinicians hemodynamic data that is considered to be the gold standard for heart-failure management.

Disclosed herein is a wireless and leadless left atrial pressure measurement device configured for delivery through a thickness of an atrial septum via a minimally invasive delivery tool. In a first embodiment, the device includes a wireless pressure sensor, a first anchoring element, and a second anchoring element. The wireless pressure sensor includes a proximal portion, a distal portion opposite the proximal portion, and a housing containing a hermetically sealed cavity containing a sensor circuit. The first anchoring element includes a first distal end and a first free proximal end generally opposite the first distal end. The first distal end is operably coupled to the wireless pressure sensor. The first anchoring element extends proximally away from the proximal portion. The second anchoring element includes a second distal end and a second free proximal end generally opposite the second distal end. The second distal end is operably coupled to the wireless pressure sensor. The second anchoring element extends proximally away from the proximal portion. When the first and second anchoring elements are free to assume a biased state, the first free proximal end and second free proximal end extend in generally opposite directions and the first anchoring element projects generally distally.

In one version of the first embodiment, the first anchoring element is configured such that, when the device is being delivered via the delivery tool, the first anchoring element is deflected away from the biased state via the delivery tool such that the first and second free proximal ends are in close proximity to each other and projecting generally proximally away from the proximal portion. In one version of the first embodiment, in the biased state, the first free proximal end is in close proximity to the distal region as compared to the second free proximal end. In one version of the first embodiment, in the biased state, the first anchoring element extends along a longitudinal side of the wireless pressure sensor offset from the longitudinal side. In one version of the first embodiment, in the biased state, the first anchoring element extends along a longitudinal side of the wireless pressure sensor offset from the longitudinal side. In one version of the first embodiment, in the biased state, the first anchoring element and the wireless pressure sensor combine to form a clamping arrangement.

In one version of the first embodiment, the clamping arrangement comprises a distance between the first anchoring element and the wireless pressure sensor that is slightly less than the thickness of the atrial septum. In one version of the first embodiment, the device further includes a silicone disc seal immediately adjacent the proximal portion and through which at least one of the first or second anchoring element extends.

In one version of the first embodiment, the device further includes a feature extending from the proximal region and configured for engagement by a tether of the delivery tool. The feature includes a knob extending from the proximal region. In one version of the first embodiment, the device further includes a feature including a knob, an extension plug and a lanyard. The lanyard is attached to the knob at one end and a second end of the lanyard is attached to the proximal region.

In one version of the first embodiment, the first anchoring element includes a biocompatible resilient material. For example, the biocompatible resilient material is selected from: platinum, NITINOL, silicone, polyurethane, plastic polyether block amide, high density polyethylene, silicone rubber, and any combination thereof. The anchoring elements may be wire, flat sheets or a host of other configurations.

In a second embodiment, the device includes a wireless pressure sensor, a first anchoring element, and a second anchoring element. The wireless pressure sensor includes a proximal portion, a distal portion opposite the proximal portion, and a housing containing a hermetically sealed cavity containing a sensor circuit. The first anchoring element is supported on the wireless pressure sensor between the proximal and distal portions and includes first and second wings spaced apart from each other. When the first and second wings are in a biased state, the first and second wings extend radially outward from the wireless pressure sensor. The second anchoring element is supported on the wireless pressure sensor between the proximal and distal portions and includes third and fourth wings spaced apart from each other. When the third and fourth wings are in a biased state, the third and fourth wings extend radially outward from the wireless pressure sensor and the third and fourth wings face the first and second wings in an opposed, spaced apart fashion.

In one version of the second embodiment, the first and second anchoring elements are configured such that, when the device is being delivered via the delivery tool, the first, second, third and fourth wings are deflected away from the biased state via the delivery tool such that the first and second wings project generally distally and the third and fourth wings project generally proximally. In one version of the first embodiment, the first anchoring element and the second anchoring element combine to form a clamping arrangement. In one version of the first embodiment, the clamping arrangement includes a distance between the first and second wings and the third and fourth wings that is slightly less than the thickness of the atrial septum.

In one version of the second embodiment, the device further includes a feature on or near the proximal region and configured for engagement by a tether of the delivery tool.

In one version of the second embodiment, the first anchoring element includes a biocompatible resilient material. For example, the biocompatible resilient material is selected from: platinum, NITINOL, silicone, polyurethane, plastic polyether block amide, high density polyethylene, silicone rubber, and any combination thereof.

Also disclosed herein is a wireless and leadless left atrial pressure sensor. In one embodiment, the sensor includes a housing, a flexible diaphragm, a sensor, and a sensor circuit. The housing contains a hermetically sealed cavity. The sealed cavity opens at an opening defined within a surface of the housing. The flexible diaphragm is sealed over the opening to complete the hermetically sealed cavity. The sensor circuit includes an induction coil, a fixed capacitor, and a moveable capacitor plate. The induction coil includes a first end and a second end. The fixed capacitor plate is electrically connected to the first end of the induction coil. The moveable capacitor plate is electrically connected to the second end of the induction coil and mechanically attached to the flexible diaphragm. The sensor circuit is contained within the hermetically sealed cavity.

In one version of the embodiment, the fixed capacitor plate and the moveable capacitor plate form a variable capacitor. The capacitance of the variable capacitor varies as a function of a deflection of the flexible diaphragm in response to a left atrial pressure on the diaphragm. The induction coil and the variable capacitor form a resonant circuit comprising a resonant frequency. The resonant frequency varies in response to a change in the left atrial pressure.

In one version of the embodiment, the left atrial pressure may be obtained using a data acquisition device including an external antenna coil. The external antenna coil magnetically couples with the induction coil of the sensor to transfer power to the sensor. The resonant frequency of the sensor is determined by an analysis of a load impedance of the sensor during the power transfer. The left atrial pressure is determined using a predetermined calibration of pressure as a function of resonance frequency.

In one version of the embodiment, the housing is constructed from a non-conductive material selected from: fused silica, quartz, ceramic, and sapphire. The diaphragm is constructed from a non-conductive material selected from: fused silica, quartz, ceramic, and sapphire.

In one version of the embodiment, the diaphragm is constructed from a conductive material selected from: highly doped silicon and titanium. The diaphragm and the moveable capacitor plate are integrated into a single structure and the diaphragm is electrically connected to the second end of the induction coil.

In one version of the embodiment, the diaphragm deflects to a maximum deflection ranging from about 1 nanometer to about 100 micrometers. In one version of the embodiment, the housing further comprises an external shape selected from: a rectangular shape, a prismatic shape, and a cylindrical shape.

Also disclosed herein is a method of implanting a wireless and leadless left atrial pressure measurement device into a left atrium of a patient. In a first embodiment, the method includes: obtaining the device comprising a sensor and at least one anchoring element, each anchoring element comprising a free end and an attached end attached to the sensor; attaching the device to a catheter comprising a catheter proximal end, a catheter distal end, and a tether protruding from the catheter distal end, wherein the tether is attached to each free end of each of the at least one anchoring elements; situating the device and the catheter within a lumen of a sheath comprising a sheath proximal end and a sheath distal end, wherein: a) the sensor is situated nearest to the sheath distal end; each of the at least one anchoring elements is in a folded configuration extending in a proximal direction within the lumen; and b) the tether extends from the free end of each of the at least one anchoring elements in a proximal direction toward the catheter; and advancing the catheter, sheath, and device through a hole formed in the atrial septum from the right atrium into the left atrium.

In one version of the first embodiment, the method further includes retracting the sheath to expose the sensor within the left atrium. In one version of the first embodiment, the method further includes retracting the catheter, sheath and device together to situate the sensor against a left wall of the atrial septum in the left atrium. In one version of the first embodiment, the method further includes retracting the sheath to expose the at least one anchoring elements, allowing the anchoring elements to elastically rebound from the folded configuration to an anchoring configuration. In one version of the first embodiment, the method further includes detaching the tether from each free end of the at least one anchoring elements, and retracting the catheter and sheath from the patient. In one version of the first embodiment, the method further includes compressing each of the at least one anchoring elements from the anchoring configuration into the folded configuration to fit the device into the sheath.

In a first embodiment, the method includes: obtaining the device comprising a sensor, at least one proximal anchoring element, and at least one distal anchoring element, each anchoring element comprising a free end and an attached end attached to the sensor; attaching the device to a catheter comprising a catheter proximal end, a catheter distal end, and a tether protruding from the catheter distal end, wherein the tether is attached to each free end of each of the at least one proximal anchoring elements; situating the device and the catheter within a lumen of a sheath comprising a sheath proximal end and a sheath distal end, wherein: a) each of the at least one distal anchoring elements is situated nearest to the sheath distal end in a first folded configuration extending in a distal direction within the lumen; b) each of the at least one proximal anchoring elements is situated in a second folded configuration extending in a proximal direction within the lumen; and c) the tether extending from the device in a proximal direction toward the catheter; and advancing the catheter, sheath, and device through a hole formed in the atrial septum from the right atrium into the left atrium.

In one version of the second embodiment, the method further includes retracting the sheath to expose the one of more distal anchoring devices within the left atrium and allowing the distal anchoring elements to elastically rebound from the first folded configuration to a first anchoring configuration. In one version of the second embodiment, the method further includes retracting the catheter, sheath and device together to situate the one of more distal anchoring devices against a left wall of the atrial septum in the left atrium. In one version of the second embodiment, the method further includes retracting the sheath to expose the at least one proximal anchoring elements, allowing the anchoring elements to elastically rebound from the second folded configuration to a second anchoring configuration. In one version of the second embodiment, the method further includes detaching the tether from the device and retracting the catheter and sheath from the patient. In one version of the second embodiment, the method further includes compressing each of the at least one distal anchoring elements into the first folded configuration and each of the at least one proximal anchoring elements into the second folded configuration to fit the device into the sheath.

Also disclosed herein is a method of retrieving a wireless and leadless left atrial pressure measurement device from a left atrium of a patient, the method comprising: advancing a snare catheter situated within a sheath into a right atrium of the patient; retracting the sheath to expose a snare loop of the snare catheter; securing the snare loop around a knob or an extension plug projecting from the device; applying traction to the knob or the extension plug using the snare catheter to withdraw a sensor of the device from the atrial septum; applying countertraction using the sheath to deform each of at least one anchoring elements of the device into a folded configuration and to situate the device within the sheath; and retracting the snare catheter, sheath, and device from the patient.

While multiple embodiments are disclosed, still other embodiments of the present disclosure will become apparent to those skilled in the art from the following detailed description, which shows and describes illustrative embodiments of the disclosure. As will be realized, the devices and methods disclosed herein are capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

The following figures illustrate various aspects of the technology disclosed herein.

Corresponding reference characters and labels indicate corresponding elements among the views of the drawings. The headings used in the figures should not be interpreted to limit the scope of the claims.

DETAILED DESCRIPTION

Provided herein in various aspects of the disclosed technology are wireless left atrial pressure (LAP) sensor devices, methods of delivering the LAP sensor devices to situate and chronically anchor the device in the left atrium/atrial septum of a patient, and methods of using the device to monitor the left atrial pressure (LAP) of the patient. In addition, a delivery/retrieval system for situating, chronically anchoring, and/or retrieving the wireless LAP sensor device is provided in various other aspects.

Figure 1:
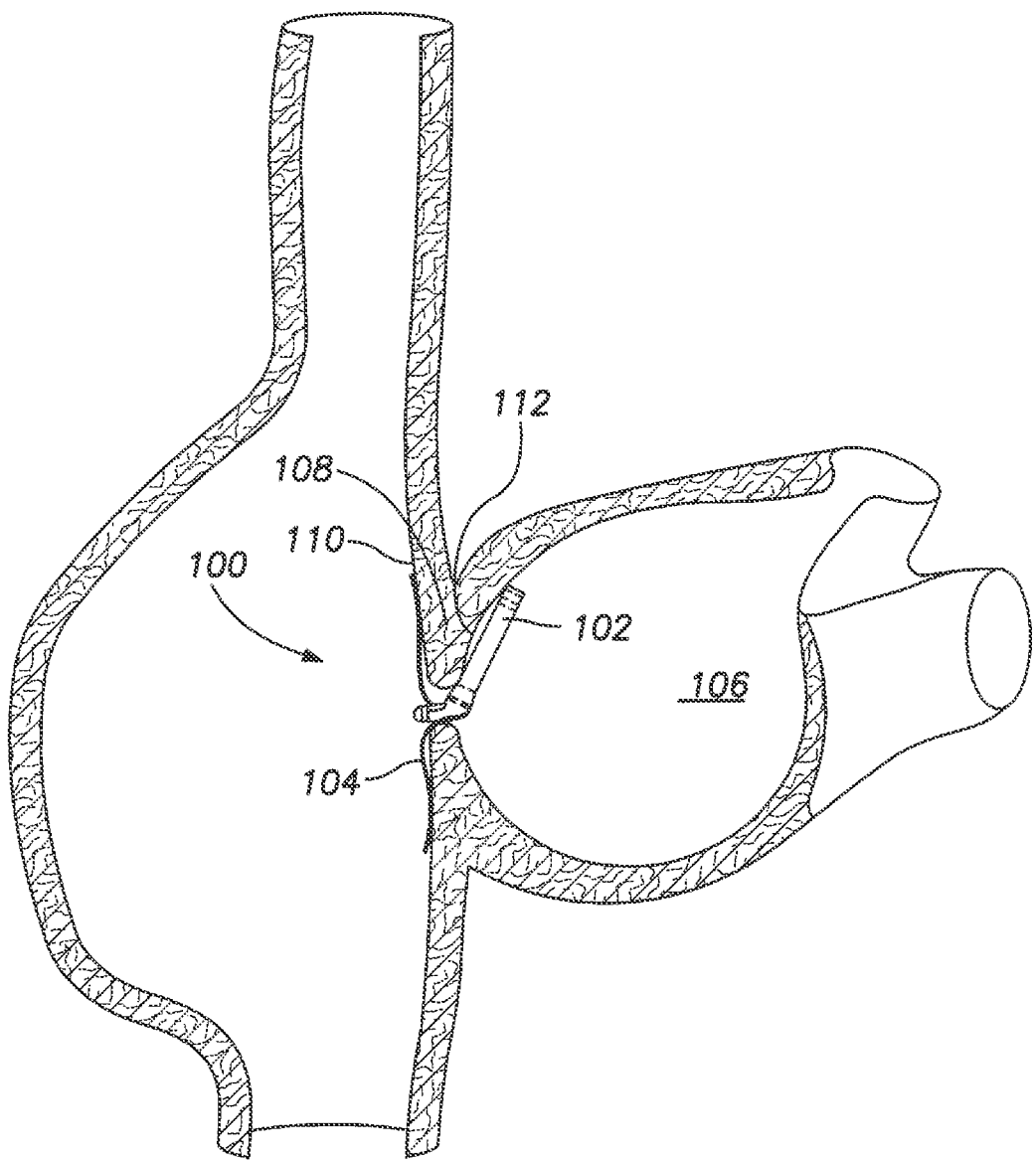
FIG. 1 is a cross-sectional view of a wireless LAP sensor device situated in a left atrium of a patient.

The wireless LAP sensor device includes a wireless LAP sensor attached to at least one anchoring element. FIG. 1 is a cross-sectional view of a wireless LAP sensor device 100 in one aspect. The wireless LAP sensor device 100 includes a sensor 102 attached to at least one anchoring element 104. At least a portion of the sensor 102 is situated within the left atrium 106 of a patient. The at least one anchoring element 104 is typically situated against the right wall 110 of the atrial septum 108 opposite to the sensor 102, as illustrated in FIG. 1. The at least one anchoring element 104 may exert a modest anchoring force against the right wall 110 to securely attach the sensor 102 to the left wall 112 of the atrial septum 108 and to prevent dislodgement or embolization of the sensor 102. In another aspect (not shown), the wireless LAP sensor device 100 may include at least one anchoring element 104 situated against the left wall 112 as well as against the right wall 110 of the atrial septum 108 to provide a more robust anchoring of the sensor 102 within the left atrium 106.

The sensor 102 incorporates circuitry (not shown) to implement capacitive pressure sensing for monitoring LAP in a patient and to further implement inductive telemetry for remotely reading the measured LAP using an external data acquisition device, which also functions as a power source for the sensor 102. The circuitry and mechanical elements of the sensor 102 further incorporate micromachined/microelectromechanical system (MEMS) elements designed to provide sensitive measurements of pressure fluctuations within the left atrium 106 housed within a relatively small implantable sensor 102.

The sensor 102 of the wireless LAP sensor device 100 may be situated and secured within the left atrium 106 using a delivery/retrieval system (not shown) to perform modifications of proven surgical implantation techniques. The sensor 102 and/or the at least one anchoring element 104 may further include radiopaque coatings, radiopaque markings, and/or other landmarks visible using one or more medical imaging methods to facilitate the visualization of the device 100 during implantation. The sensor 102 and at least one anchoring element 104 may be further designed to be readily snagged, repositioned, and/or retrieved from the left atrium/septum of the patient using the delivery/retrieval system to implement additional modifications of proven surgical remediation and/or retrieval techniques.

Because inductive telemetry is used by the circuitry of the wireless LAP sensor device 100, electrical power is supplied to the sensor 102 via inductive power transfer by the external data acquisition device. Because this inductive power transfer obviates the need for a conventional power source such as a battery or other electrical power source resident within the sensor 102 or electrically connected to the sensor 102 via electrical leads, the wireless LAP sensor device 100 may remain fully operational over extended and chronic residence periods within the left atrium 102 of the patient. In addition, the circuitry of the wireless LAP sensor device 100 may be designed to be compatible with more than one type of data acquisition device to enhance the operational flexibility of the device 100.

Various aspects of the wireless LAP sensor device 100 including the sensor 102 and at least one anchoring element 104 are described in further detail herein below. In addition, methods of implanting and or situating the wireless LAP sensor device 100 into the left atrium 106 of a patient, and methods of repositioning and/or retrieving the wireless LAP sensor device 100 from the left atrium 106 of the patient using the delivery/retrieval system are also described in further detail herein below. Methods for monitoring LAP in a patient using the implanted wireless LAP sensor device 100 are also described in further detail herein below.

I. Wireless Left Atrial Pressure (LAP) Sensor Device

In various aspects, the wireless LAP sensor device 100 includes a sensor 102 attached to at least one anchoring element 104. The sensor 102 is situated within the left atrium 106 of a patient, typically against the left wall 112 of the atrial septum 108, as illustrated in FIG. 1. The sensor 102 is secured in place by the anchoring elements 104, which may be situated against the right wall 110 of the atrial septum 108, as illustrated in FIG. 1, and optionally against the left wall 112 of the atrial septum 108 in other aspects.

In one aspect, the sensor 102 situated in the left atrium 106 may be designed to have a relatively low profile against the left wall 112 of the atrial septum 108, as illustrated in FIG. 1. This low-profile sensor design, including, but not limited to rectangular or prismatic shapes, may reduce the formation of blood clots within the left atrium 106 and may enhance the build-up of a biological layer of endothelial cells (i.e., "the intima") over the sensor 102 and the anchoring elements 104. As a result, the likelihood of blood clots forming and breaking loose may be significantly reduced as compared to sensor designs that protrude relatively deeply into the left side of the heart. Blood clots breaking loose in the left side of the heart may travel to other areas of the body such as the brain and cause a blockage in a blood vessel (i.e., an embolism). The buildup of the intima may also reinforce the attachment of the sensor 102 and the anchoring elements 104 to the atrial septum 108. As a result, the sensor 102 may be attached to the heart in a sufficiently stable manner so as to prevent injury to the heart.

Referring again to FIG. 1, the wireless LAP sensor device 100 may be inserted through the atrial septum 108 in the region of the fossa ovalis in one aspect. The fossa ovalis is typically the thinnest section of the atrial septum and therefore provides a region amenable to septal puncture as part of the implantation of the wireless LAP sensor device 100. In one aspect, the sensor 102 of the wireless LAP sensor device 100 may be situated entirely within the left atrium 106 as illustrated in FIG. 1. In other aspects, the sensor 102 may protrude into the atrial septum 108, the right atria, and other regions of the heart of the patient.

Figure 3:
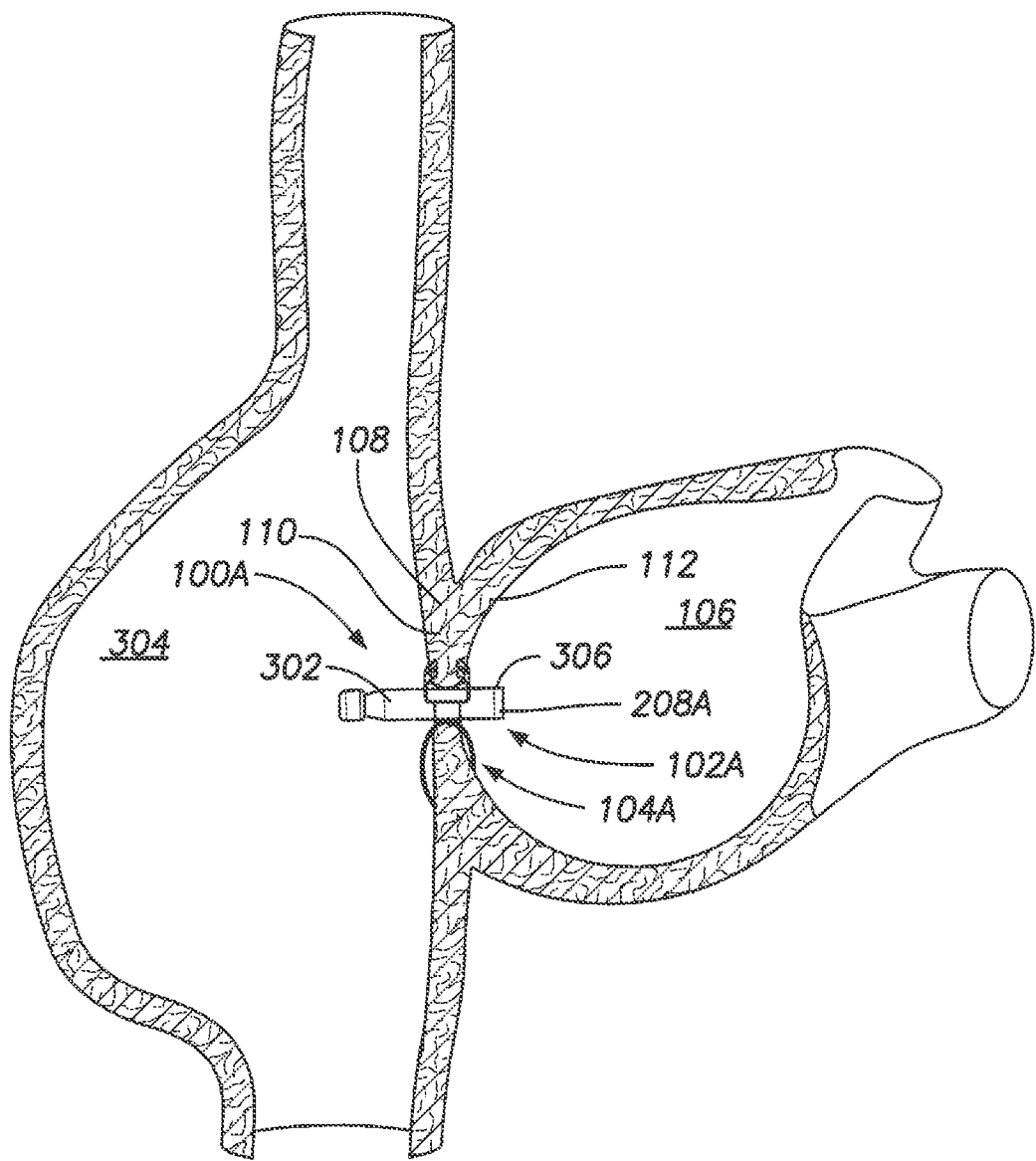
FIG. 3 is a cross-sectional view of a cylindrical wireless LAP sensor device situated in a left atrium of a patient.

FIG. 3 is a cross-sectional view of a wireless LAP sensor device 100A in another aspect. In this other aspect, the device 100A may include a cylindrical sensor 102A that includes a proximal sensor end 302 projecting into the right atrium 304 and a distal sensor end 306 projecting into the left atrium 106 as illustrated in FIG. 3. In this aspect, the distal sensor end 306 may include a diaphragm 208A exposed to the blood pressure within the left atrium 106. Also in this aspect, the sensor 102A may be held in place by anchoring elements 104A situated against the right wall 110 and the left wall 112 of the atrial septum 108. The anchoring elements 104A situated in this manner may provide more robust anchoring forces for the cylindrical sensor 102A in this aspect; the cylindrical sensor 102A may be larger and/or heavier than the rectangular sensor 102 illustrated in FIG. 1.

Figure 2:
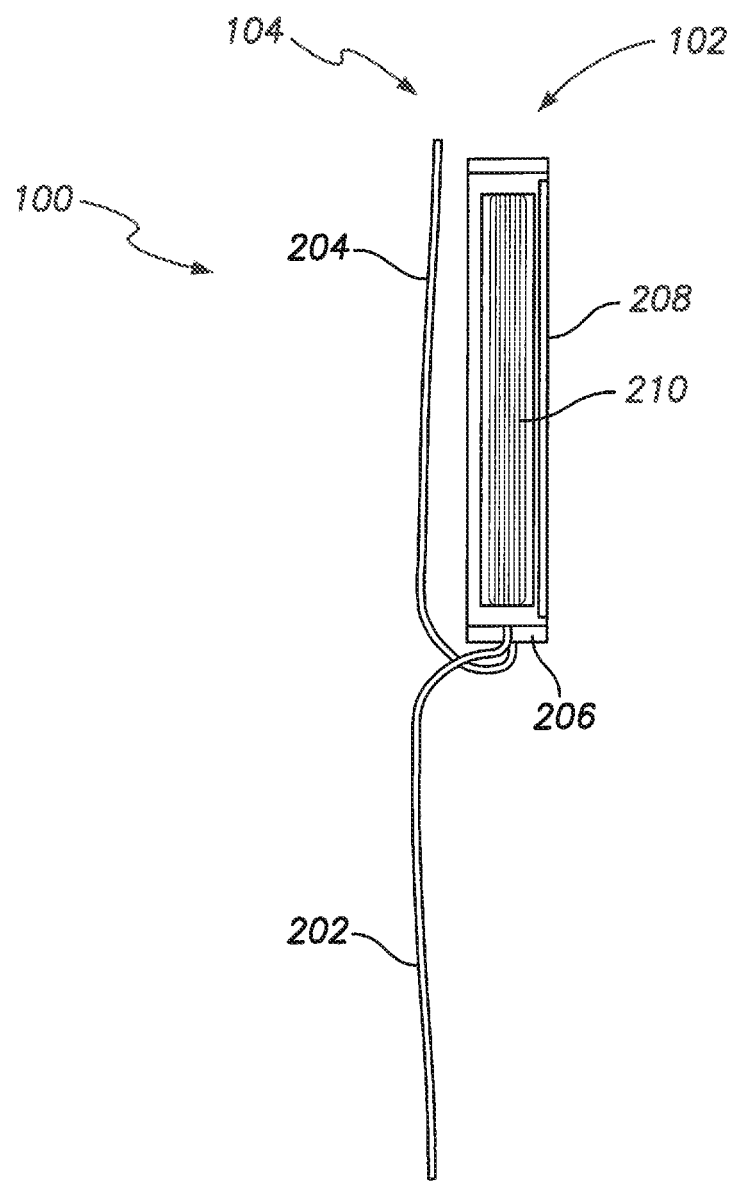
FIG. 2 is a side cross-sectional view of a wireless LAP sensor device with a pair of anchoring elements.

FIG. 2 is a side cross-sectional view of the rectangular sensor 102 and the anchoring elements 104 of the wireless LAP sensor device 100 illustrated previously in FIG. 1. The sensor 102 may include a housing 206 containing a sensor circuit 210 connected to a deformable diaphragm 208. The diaphragm 208 is typically exposed to the blood pressure within the left atrium (not shown). Left atrial pressure (LAP) within the left atrium typically exerts a force against the diaphragm 208, causing the deflection of the diaphragm 208. The sensor circuit 210 is designed to detect changes in the deflection of the diaphragm 208 resulting from changes in LAP and to encode those detected changes into a form that may be read by an external data acquisition device through a process of inductive telemetry. The LAP measurements from the sensor 102 may provide valuable information for diagnosing a variety of cardiac problems including, but not limited to mitral stenosis and left ventricle failure associated with high LAP. The design and operation of the sensor circuit 210 are described in more detail herein below.

Referring again to FIG. 2, one or more anchoring elements 104 may be attached to the housing 206 of the sensor 102. In one aspect, the anchoring elements 104 may include a first anchoring element 202 and a second anchoring element 204 as illustrated in FIG. 2. The anchoring elements 104 are typically formed from a biodegradable and resilient material capable of being reversibly deformed into a compact folded configuration (not shown) during implantation of the wireless LAP sensor device 100, typically accomplished using catheter-based surgical methods. In addition, the anchoring elements 104 are designed to revert into an anchoring configuration as illustrated in FIG. 2, typically by elastic rebound of the anchoring elements 104 from their folded configuration.

To facilitate the reversible elastic deformation of the anchoring elements 104 into the folded configuration and back into the anchoring position, the anchoring elements 104 may be formed from biocompatible and elastically deformable materials including, but not limited to, memory materials such as NITINOL. In addition, the anchoring elements 104 may be shaped and dimensioned to provide relatively flexible sub-structures including, but not limited to: loops, lobes, and/or arms formed from wires and/or thin sheets of a biocompatible and elastically deformable material. A detailed description of the design and construction of the anchoring elements 104 in various other aspects is provided herein below.

a. Anchoring Elements

Figure 4:
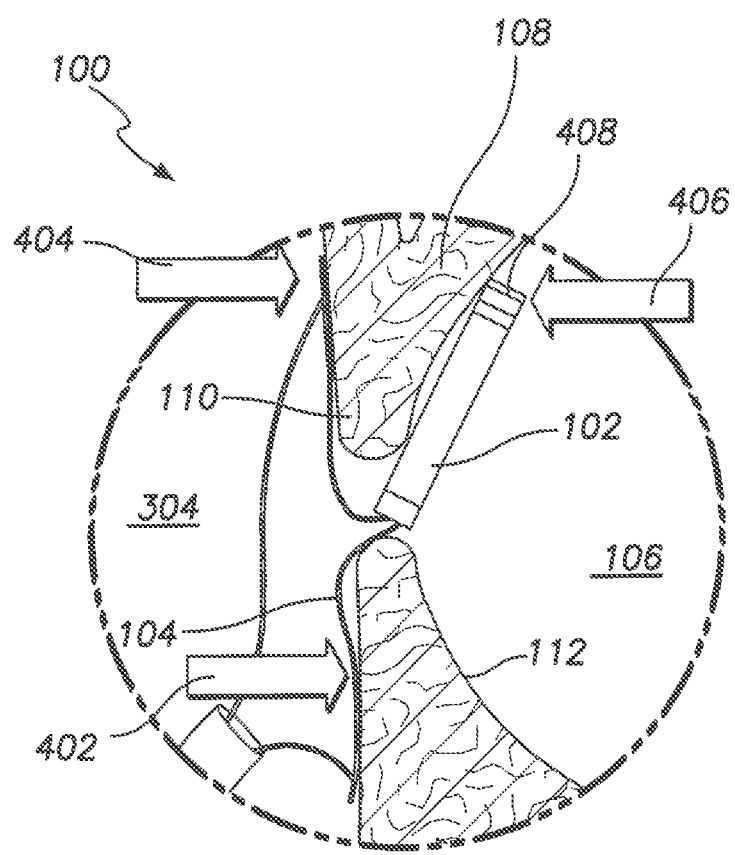
FIG. 4 is a cross-sectional view of a wireless LAP sensor device situated in a left atrium of a patient showing the anchoring forces generated by the anchoring elements and sensor.

In various aspects, the wireless LAP sensor device 100 includes at least one anchoring element 104 to secure the sensor 102 firmly in place within the left atrium 106 as described previously. The anchoring elements 104 may be situated against the right wall 110 of the atrial septum 108, against the left wall 112 of the atrial septum 108, or against both the right wall 110 and the left wall 112 of the atrial septum 108. FIG. 4 is a close-up cross-sectional view of a wireless LAP sensor device 100 situated within the heart of a patient, showing the anchoring forces that secure the sensor 102 firmly in place within the left atrium 106 in one aspect. The anchoring elements 104 typically press against the left wall 112 and/or right wall of the atrial septum 108. The forces 402 and 404 generated against the right wall 110 by the anchoring elements 104 situated within the right atrium 304 may be resisted by an opposing force 406 generated against the left wall 112 by either additional anchoring elements 104 (not shown) situated within the left atrium 106 and/or a surface 408 of the sensor 102 situated adjacent to the left wall 112. These opposed anchoring forces 402, 404, and 406 compress the atrial septum 108 and maintain the sensor 102 in place within the left atrium 106. In various aspects, the separation distance between the base of the at least one anchoring element 104 and the additional anchoring elements 104 and/or surface 408 of the sensor 102 may be slightly less than the typical thickness of the atrial septum 108 and/or the fossa ovalis.

i. Profile and Curvature Along Length of Anchoring Elements

In an aspect, the anchoring elements 104 are designed to be compatible with the delivery/retrieval system. In particular, the anchoring elements 104 may be dimensioned to fit within a sheath of an introductory catheter in a folded configuration. Typically, the folded anchoring elements 104 may be situated proximally and/or distally to the sensor 102, depending on the particular design of the wireless LAP sensor device 100. As a result, the anchoring elements 104 may each consist of an elongated and narrow structure. In an aspect, each anchoring element 104 may have a general shape or profile including, but not limited to a flattened lobe, a flattened petal, or a flattened tine.

Figure 5:
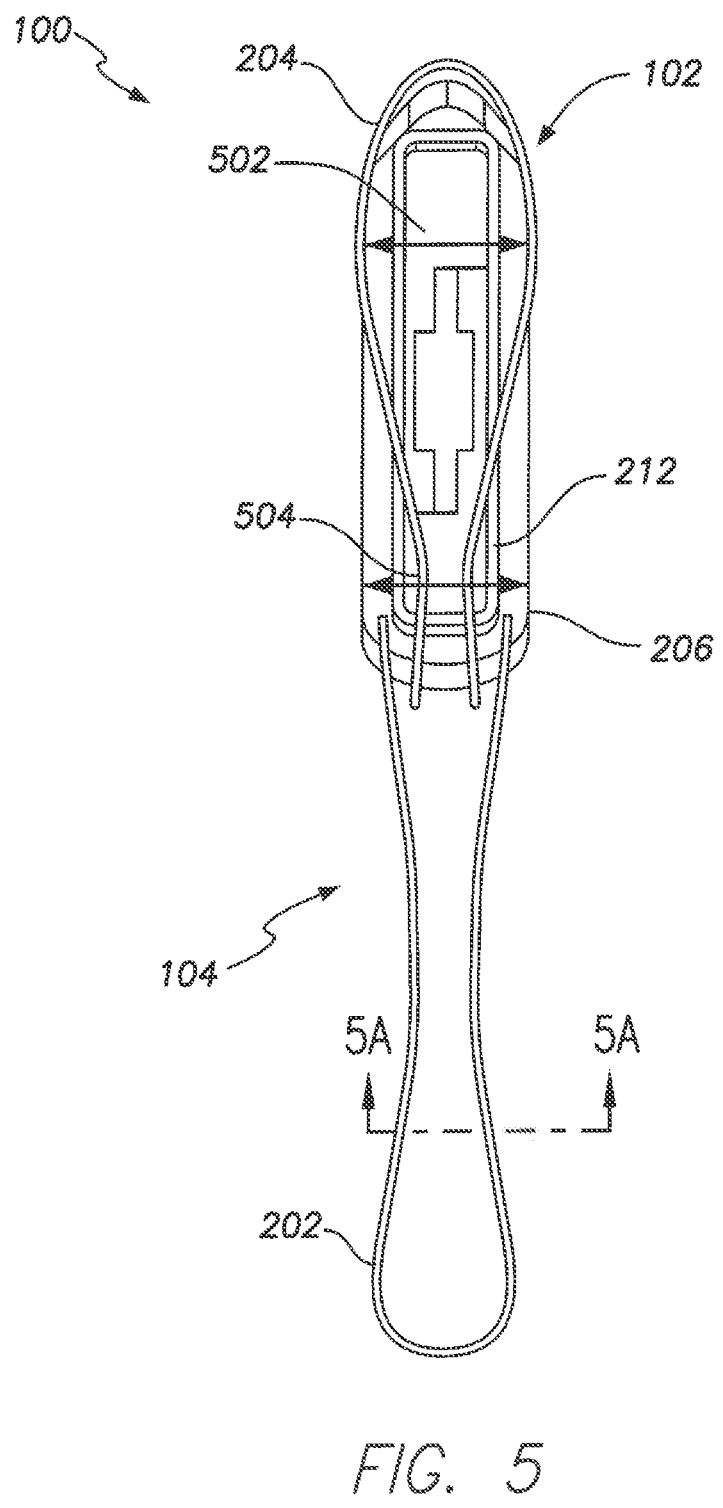
FIG. 5 is a side view of the wireless LAP sensor device illustrated in FIG. 2 showing anchoring elements in the form of wire frames.

FIG. 5 is a side view of the wireless LAP sensor device 100 illustrated previously in FIG. 2. In this aspect, each anchoring element 202 and 204 may have a flattened lobe profile, as illustrated in FIG. 5. In order to fit within the sheath of an introductory catheter in a folded configuration, each anchoring element 202 and 204 may have a maximum width 502 that is comparable to the sensor width 504. In another aspect (not shown), the maximum width 502 of each anchoring element 202 and 204 may be significantly wider than the sensor width 504. In this other aspect, the lobe profile of each anchoring element 202 and 204 may be compressed laterally within the sheath of the delivery catheter in the folded configuration and may then expand to its full width upon release from the sheath and subsequent reversion to the anchoring configuration. As illustrated in FIG. 5, each anchoring element 104 is typically rounded at its free end to avoid injury to the atrial septum 108 during implantation and subsequent residence in the heart of the patient.

Referring back to FIG. 4, each anchoring element 104 may further include a curvature along its length. In the anchoring configuration, this curvature may impart a spring functionality to each anchoring element 104, allowing each anchoring element 104 to exert a force against the atrial septum 108. Each anchoring element 104 may be provided with a curvature in any profile capable of imparting the spring functionality to the anchoring element 104 including, but not limited to a C-shaped profile, an S-shaped profile, a circular arc profile, and any other suitable curvature profile.

ii. Wire-Frame Anchoring Elements

Figure 5A:
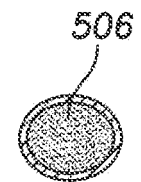
FIG. 5A is a cross-sectional view of an anchoring element of FIG. 5.

Referring back to FIG. 5, each anchoring element 104 may be constructed from a thin elongate stock formed from a resilient material including but not limited to a wire, resulting in an anchoring element 104 in the form of a wire frame in various aspects. In an aspect, the cross-sectional profile of the wire may be any known shape including, but not limited to a round profile 506, as illustrated in FIG. 5A, or an elliptical, semi-circular, square, rectangular, triangular, or any other polygonal cross-sectional profile. In additional aspects, the cross-sectional profile of the wire may be solid or hollow. In other aspects, the material forming each anchoring element 104 may be cut from a sheet of a suitable material in the desired profile shape; in these other aspects, the material of each anchoring element 104 may resemble a wire with a rectangular or square cross-sectional profile.

iii. Solid Sheet Anchoring Elements

Figure 6A:
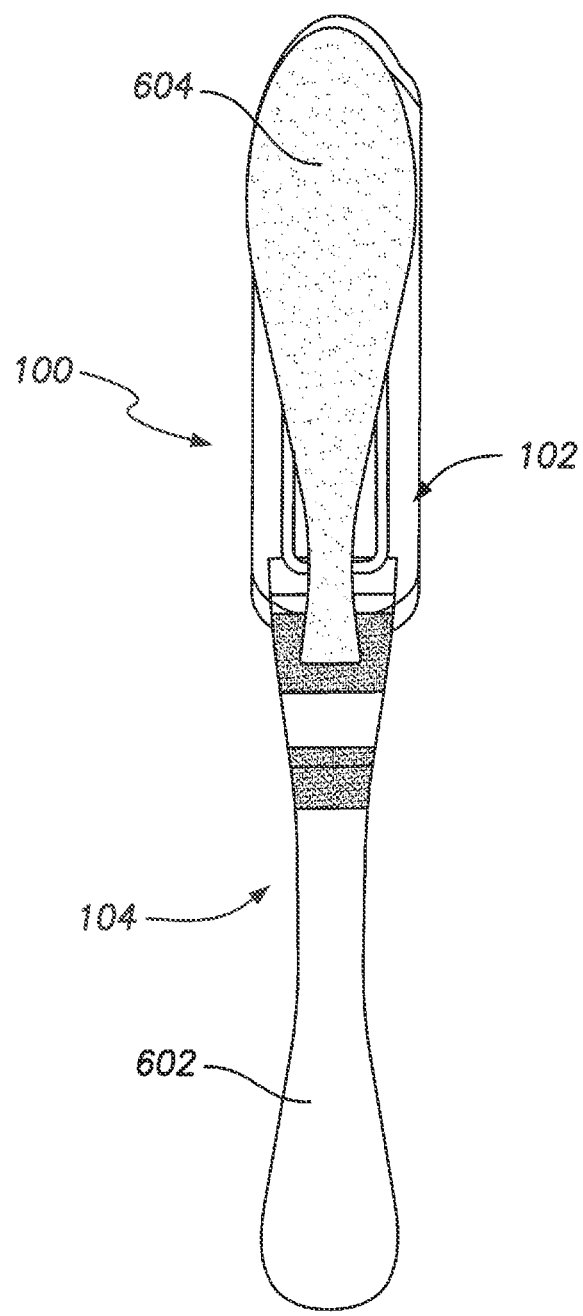
FIGS. 6A and 6B are a side view and a perspective view of a wireless LAP sensor device with anchoring elements in the form of thin sheets.
Figures 6B, 6C:
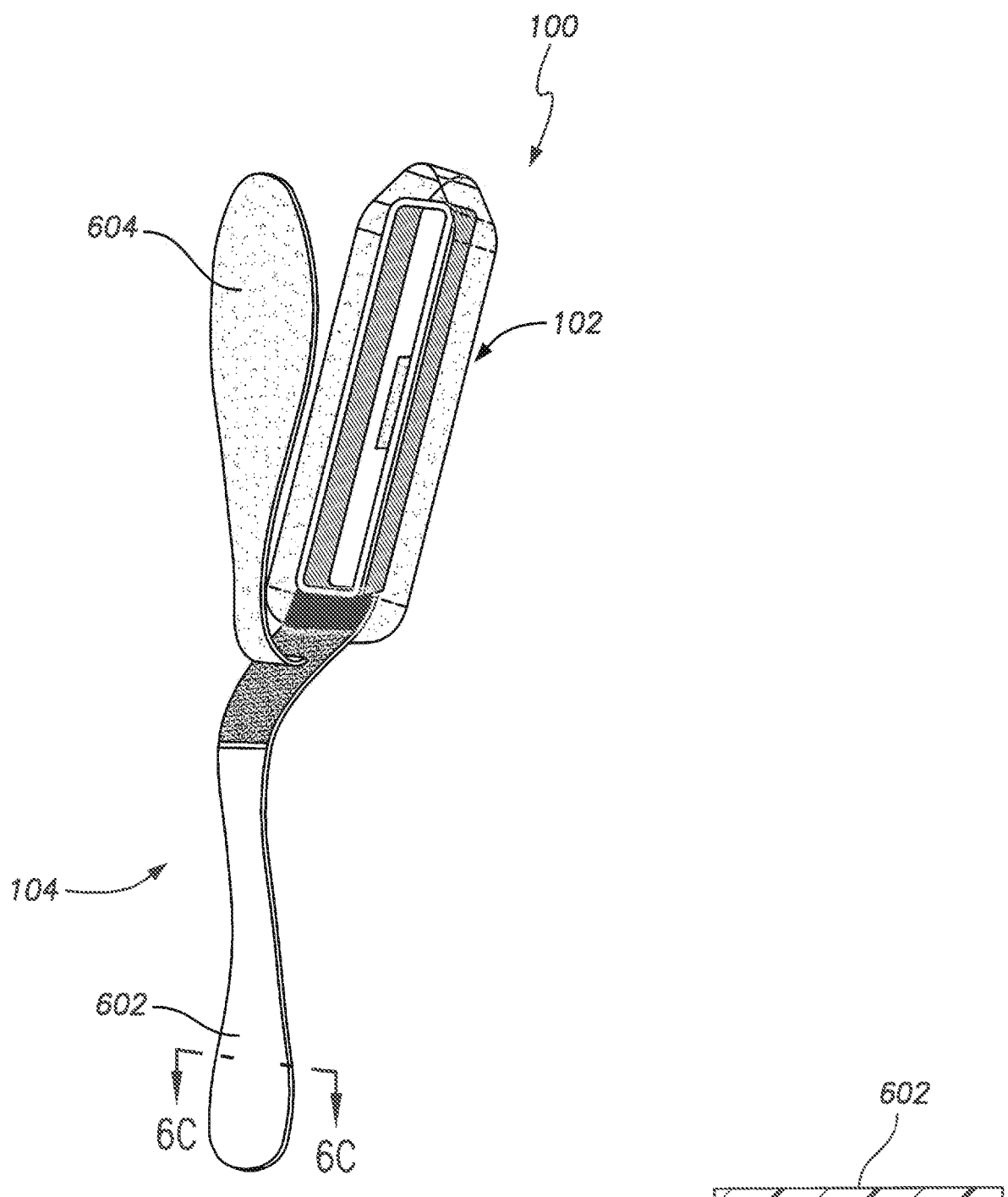
FIG. 6C is a linear profile of an anchoring element of FIGS. 6A and 6B.

In other aspects, the one or more anchoring elements 104 may be provided in alternative forms to a wire frame form. FIG. 6A is a side view and FIG. 6B is a perspective view of a wireless LAP sensor device 100 in another aspect. In this aspect, each anchoring element 104 may be provided in the form of a solid sheet of a resilient material, resulting in paddle-like anchoring elements 602 and 604. These paddle-like anchoring elements 602 and 604 may have lobe-like profiles and curvatures similar to the wire frame anchoring elements 202 and 204 illustrated in FIG. 5. However, the added material and contact area of the paddle-like anchoring elements 602 and 604 relative to the wire frame anchoring elements 202 and 204 may impart additional anchoring force capability to the paddle-like anchoring elements 602 and 604.

Figure 7A:
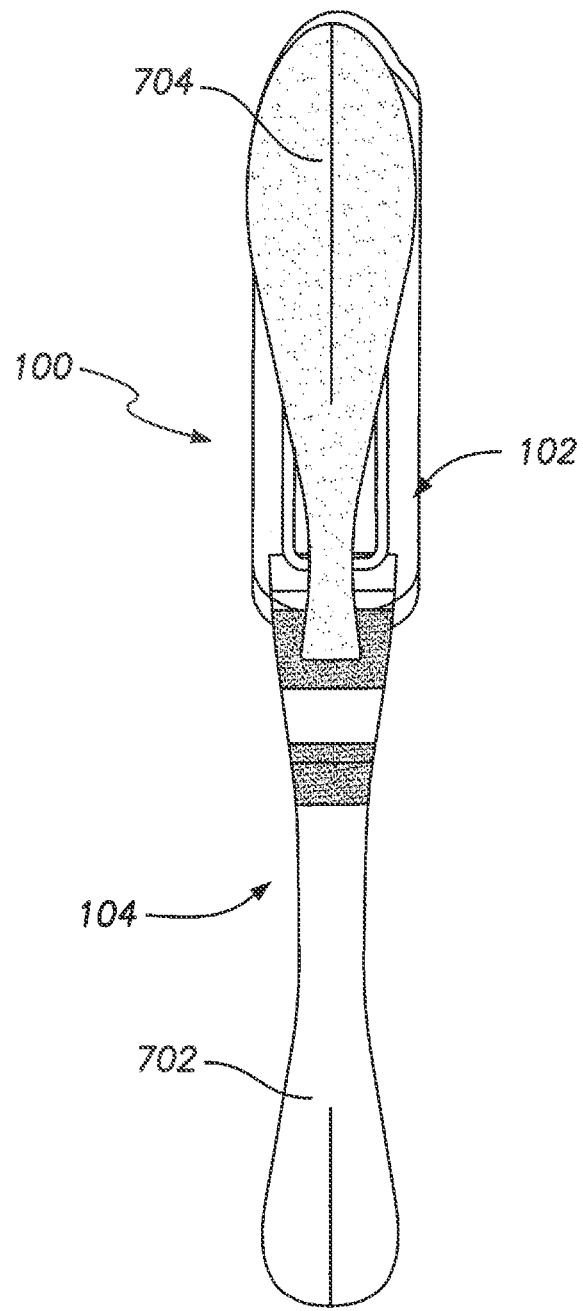
FIG. 7A and FIG. 7B are a side view and a perspective view of a wireless LAP sensor device with spoon-like anchoring elements.
Figures 7B, 7C:
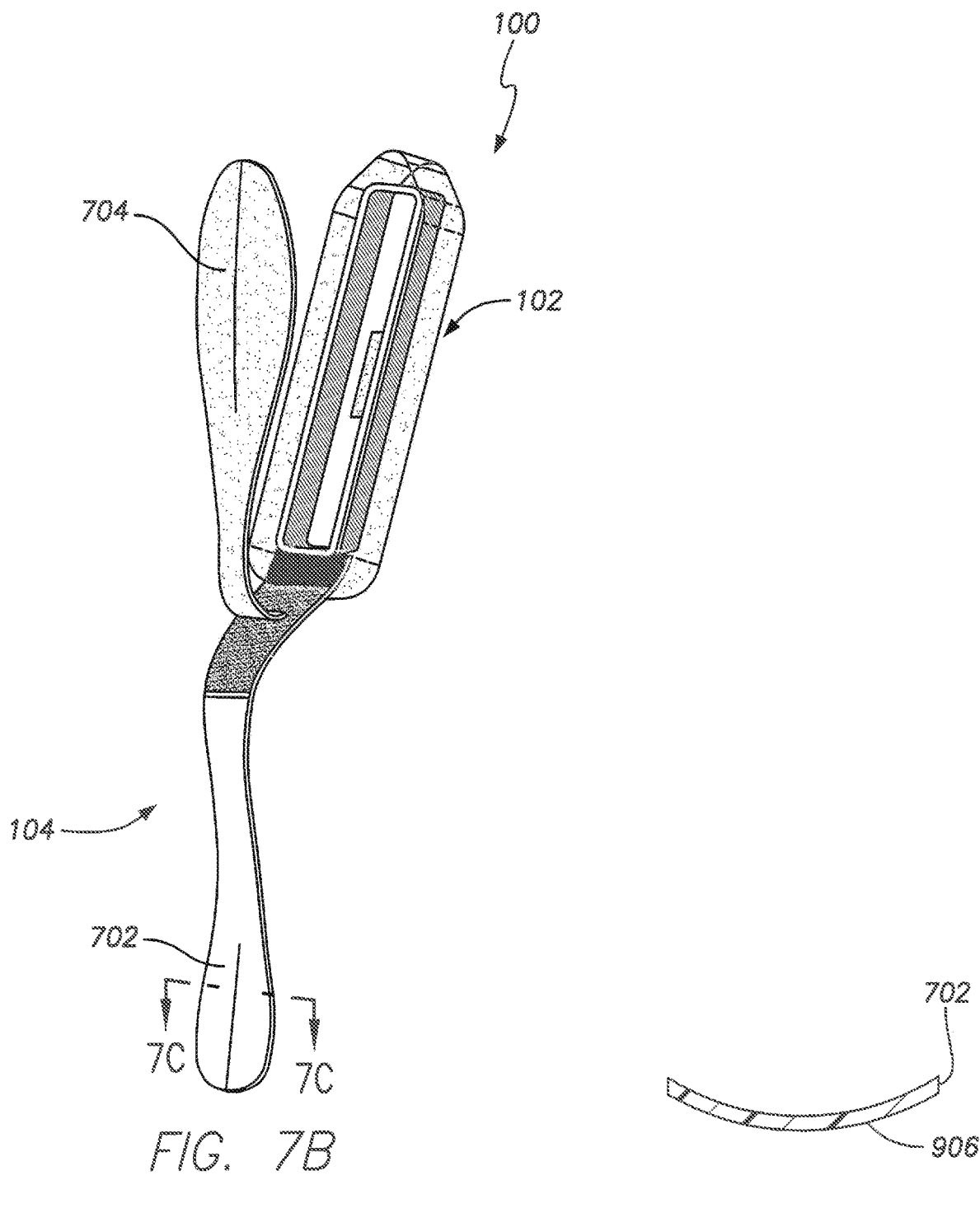
FIG. 7C is a curved profile of an anchoring element of FIGS. 7A and 7B.

The paddle-like anchoring elements 602 and 604 may possess a curvature along the length of these anchoring elements 602 and 604 to impart a spring functionality, but may retain a longitudinal cross-section that is essentially planar, as illustrated in FIG. 6C. In other aspects, the anchoring elements 104 may have non-linear longitudinal cross-sections. FIG. 7A is a side view and FIG. 7B is a perspective view of a wireless LAP sensor device 100 in which the longitudinal cross-section of the anchoring elements 104 is formed into a curved profile as illustrated in FIG. 7C, resulting in spoon-like anchoring elements 702 and 704. The curved profile may be oriented such that the outer curve 706 is facing away from the atrial septum as illustrated in FIG. 7; in this aspect, the curved profile may enhance the mechanical strength of the anchoring elements 702 and 704. In another aspect, the curved profile may be oriented such that the outer curve 706 is facing away from the atrial septum (not shown) which may enhance the contact area between the anchoring elements 104 and the atrial septum. In other additional aspects, the longitudinal cross-section of the anchoring elements 104 may be provided in other forms including, but not limited to: a creased profile such as a "V-shaped" profile in which two planar segments intersect at an angle along a crease line; a polygonal profile in which multiple planar segments intersect at multiple crease lines; a pleated profile such as a "W-shaped" profile; a recurved or saddle-shaped profile, and any other longitudinal cross-section without limitation.

In other aspects, the solid sheet forms of the anchoring elements 104 illustrated in FIGS. 6-7 and discussed herein above may further include one or more discontinuities in the solid sheet form including, but not limited to: holes, voids, openings, serrations, indentations and or protrusions along the lateral edges of the anchoring elements 104, and any other discontinuity in the solid sheet material used to form the anchoring elements 104. These discontinuities may be provided to enhance the function of the anchoring elements 104 in one or more of at least several different manners including, but not limited to: providing local flexibility in a desired region of an anchoring element 104; providing a surface texture that enhances the anchoring force provided by the anchoring element 104; providing a surface texture that inhibits the formation of blood clots and/or enhanced the adhesion of epithelial cells and formation of the intima; providing one or more reservoirs for the release of active compounds such as anti-inflammatory compounds, and any combination thereof. In yet other aspects, the one or discontinuities in the solid sheet form may include additional materials including, but not limited to: local reinforcing members attached to a region of an anchoring member; protruding surface textural elements such as protrusions, bumps, ridges, and other textural elements, and any combination thereof.

iv. Construction of Anchoring Elements

The anchoring elements 104 may be constructed using any biocompatible resilient material without limitation. Non-limiting examples of suitable biocompatible resilient materials include metals such as platinum, metal alloys such as stainless steel, memory materials such as NITINOL, silicone, polyurethane, plastic polyether block amide, high density polyethylene, silicone rubber, and any other known biocompatible resilient material. In one aspect, the anchoring elements 104 may be constructed using a memory material such as NITINOL by etching a desired anchoring arm 104 shape from a single sheet of material, heat-forming a NITINOL wire or other form into a desired anchoring arm 104 shape, or any combination thereof.

In other aspects, at least a portion of each anchoring element 104, and or a portion of the one or more anchoring elements 104 may be constructed using a biodegradable material. In these other aspects, the biodegradable materials may be incorporated to provide for the removal of the wireless LAP sensor device 100 after implantation. In other additional aspects, the biodegradable materials may be incorporated as a coating over the anchoring elements 104 to provide additional functionality including, but not limited to: enhanced biocompatibility, timed release of active compounds such as anti-inflammatory compounds, and any combination thereof.

v. Number and Arrangement of Anchoring Elements

Figure 8:
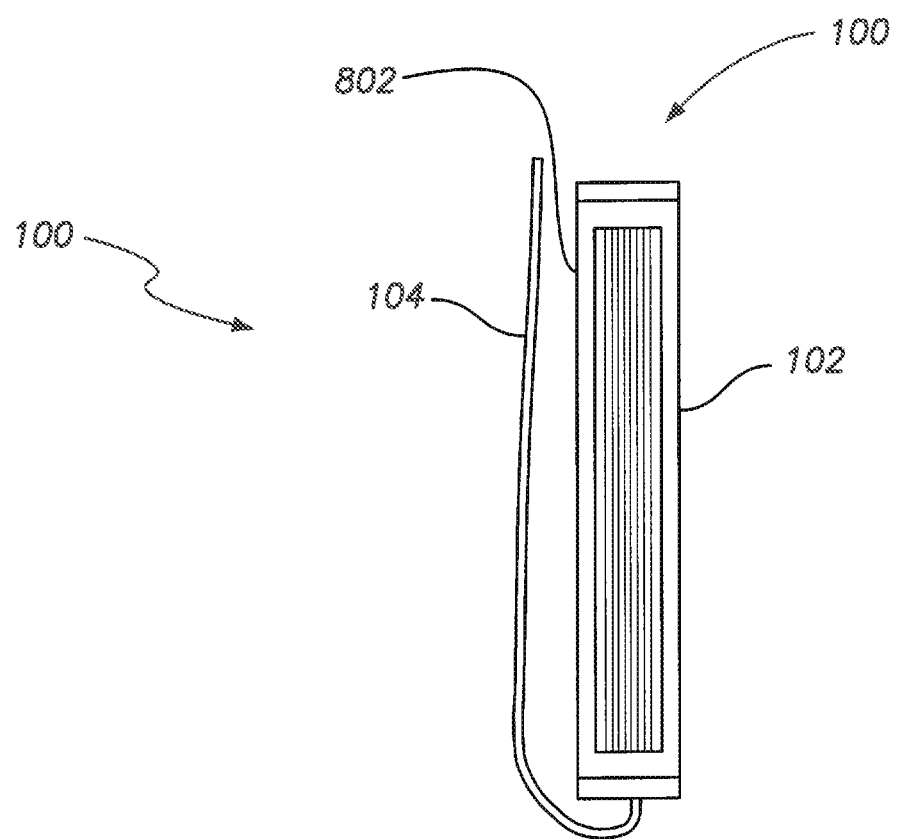
FIG. 8 is a side view of a wireless LAP sensor device that includes a single anchor element.

In various aspects, the wireless LAP sensor device 100 may include any number of anchoring elements 104 without limitation. In various aspects illustrated in FIGS. 1, 2, and 4-7 and described previously herein, the wireless LAP sensor device 100 may include a pair of anchoring elements 104 in various forms. FIG. 8 is a side view of a wireless LAP sensor device 100 in one aspect that includes a single anchor element 104. In this aspect, the single anchor element 104 and the back surface 802 of the sensor 102 exert opposing anchoring forces that compress the atrial septum (not shown) and maintain the sensor 102 in a fixed position within the left atrium (not shown) of the patient.

In other aspects, the wireless LAP sensor device 100 may include between one and about twelve anchoring elements 104. In one aspect, the anchoring elements 104 may be situated against the right wall of the atrial septum, against the left wall of the atrial septum, or against both the left and right walls of the atrial septum 108. In another aspect, the anchoring elements situated against one of the walls of the atrial septum may be uniformly distributed about an axis perpendicular to the surface of the wall. For example, the two anchoring elements 104 illustrated in FIG. 1 are separated by an angle of 180 degrees about an axis perpendicular to the right wall 110 of the atrial septum 108.

Figure 9A:
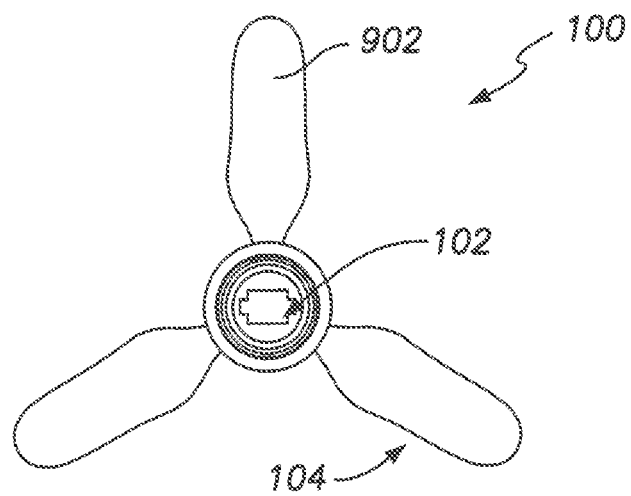
FIG. 9A is an end view and FIG. 9B is a side view of a wireless LAP sensor device that includes a "dual propeller" arrangement of six anchoring elements.
Figure 9B:
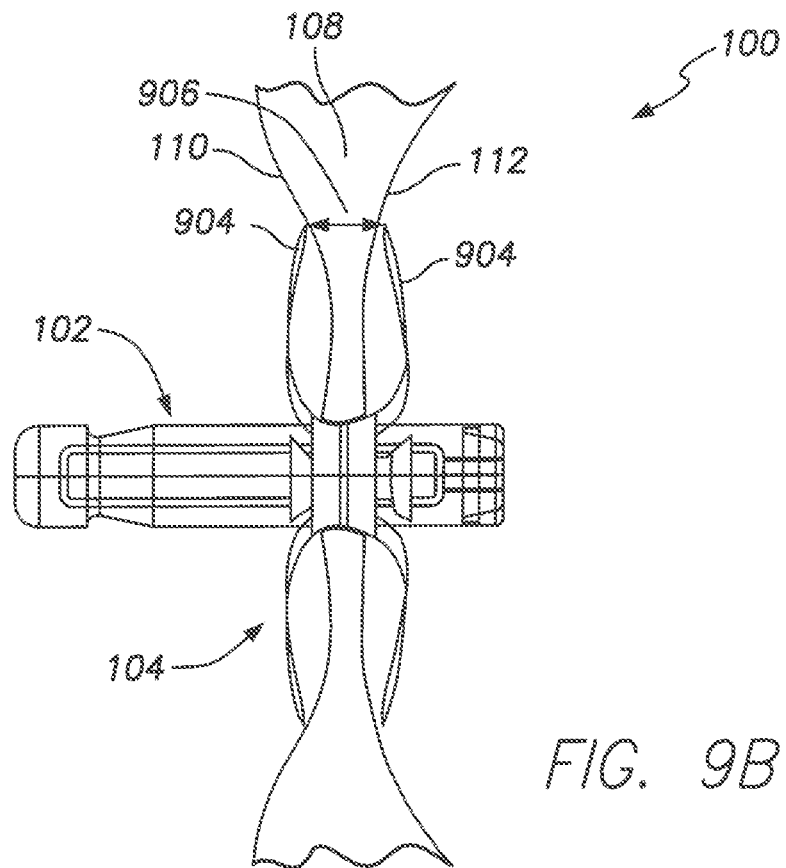

FIG. 9A is an end view and FIG. 9B is a side view of a wireless LAP sensor device 100 that includes a "dual propeller" arrangement of six anchoring elements 104: a set of three proximal anchoring elements 902 and a set of three distal anchoring elements 904. Referring to FIG. 9A, the proximal anchoring elements 902 are distributed at even angular intervals about an axis perpendicular to the right wall 110 of the atrial septum 108. In this aspect, the proximal anchoring elements 902 are situated against the right wall 110 of the atrial septum 108 and the distal anchoring elements 904 are situated against the left wall 110 of the atrial septum 108. The anchoring forces in this aspect are provided by the anchoring elements 104, rather than by a combination of the anchoring elements 104 and a surface of the sensor 102 as in the various aspects described previously herein in which all anchoring elements were situated against the right wall 110 of the atrial septum 108.

When the anchoring elements 104 are in the extended anchoring position pressing against the atrial septum 108, the proximal anchoring elements 902 and the distal anchoring elements 904 may be spaced apart at a distance 906 approximately equal to the thickness of the atrial septum 108 in the area of the implanted wireless LAP sensor device 100. For example, if the device 100 is implanted in the region of the fossa ovalis the separation distance 906 may be about 3-4 mm. In an aspect, a biasing mechanism may be provided to provide a force to pull the proximal anchoring elements 902 and the distal anchoring elements 904 together to enhance the anchoring forces provided by the anchoring elements 104. The biasing mechanism may be adapted to press the proximal anchoring elements 902 and/or distal anchoring elements 904 against the walls of the atrial septum 108.

In one aspect, the biasing mechanism may be a spring mechanism that provides pressure on the walls of the atrial septum 108 and pulls the proximal anchoring elements 902 and/or distal anchoring elements 904 flat against the atrial septum 108 to maintain a low profile for the anchoring elements 104 and the sensor 102. The spring mechanism may include a metal spring, a spring made from other materials with strong material memory, and any other suitable spring. In an aspect, the spring may be constructed from a material including, but not limited to MP35N, nickel chrome alloys or other suitable biocompatible materials.

The implantation of the wireless LAP sensor device 100 in this aspect is accomplished using additional modifications of the catheter-based implantation methods to provide for the situation of the atrial septum between the proximal anchoring elements 902 and the distal anchoring elements 904. The method of implanting the wireless LAP sensor device 100 that includes the dual propeller arrangement of anchoring elements 104 is described in further detail herein below.

Figure 10:
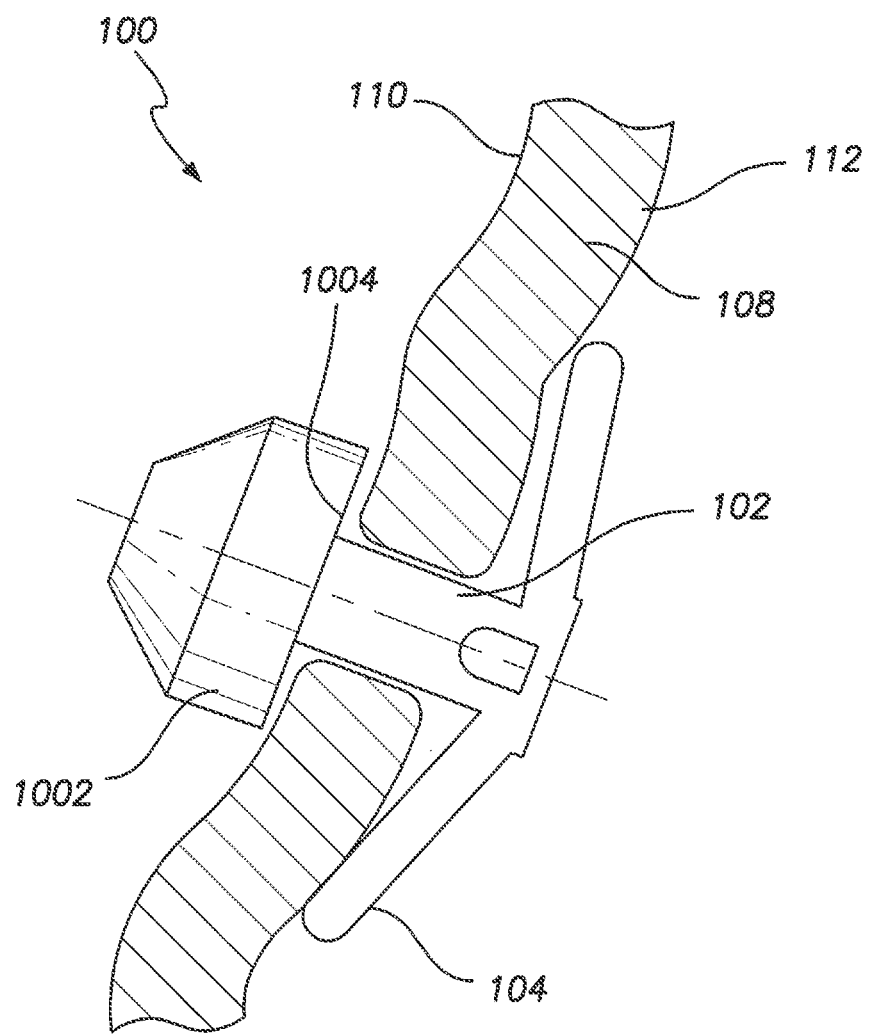
FIG. 10 is a side view of a wireless LAP sensor device that includes four anchoring elements situated against the left wall of the atrial septum.

FIG. 10 is a side view of a wireless LAP sensor device 100 in an additional aspect that includes four anchoring elements 104 situated against the left wall 112 of the atrial septum 108. In this additional aspect, the anchoring is further provided by an enlarged proximal segment 1002 of the sensor 102 defining a flattened proximal face 1004. The proximal face 1004 is situated against the right wall 110 of the atrial septum 108 and generates an anchoring force opposite to the anchoring forces generated by the four anchoring elements 104. In one aspect, the proximal face 1004 may have a width of 0.25 mm to 4 mm to provide a surface onto which the atrial septum 108 may be pressed to clamp the atrial septum 108 in place in relation to the sensor 102. In addition to providing a robust clamping surface for anchoring the device 100, the enlarged proximal segment 1002 may also impede any potential embolization of the device 100 within the left atrium of the patient.

Figure 11:
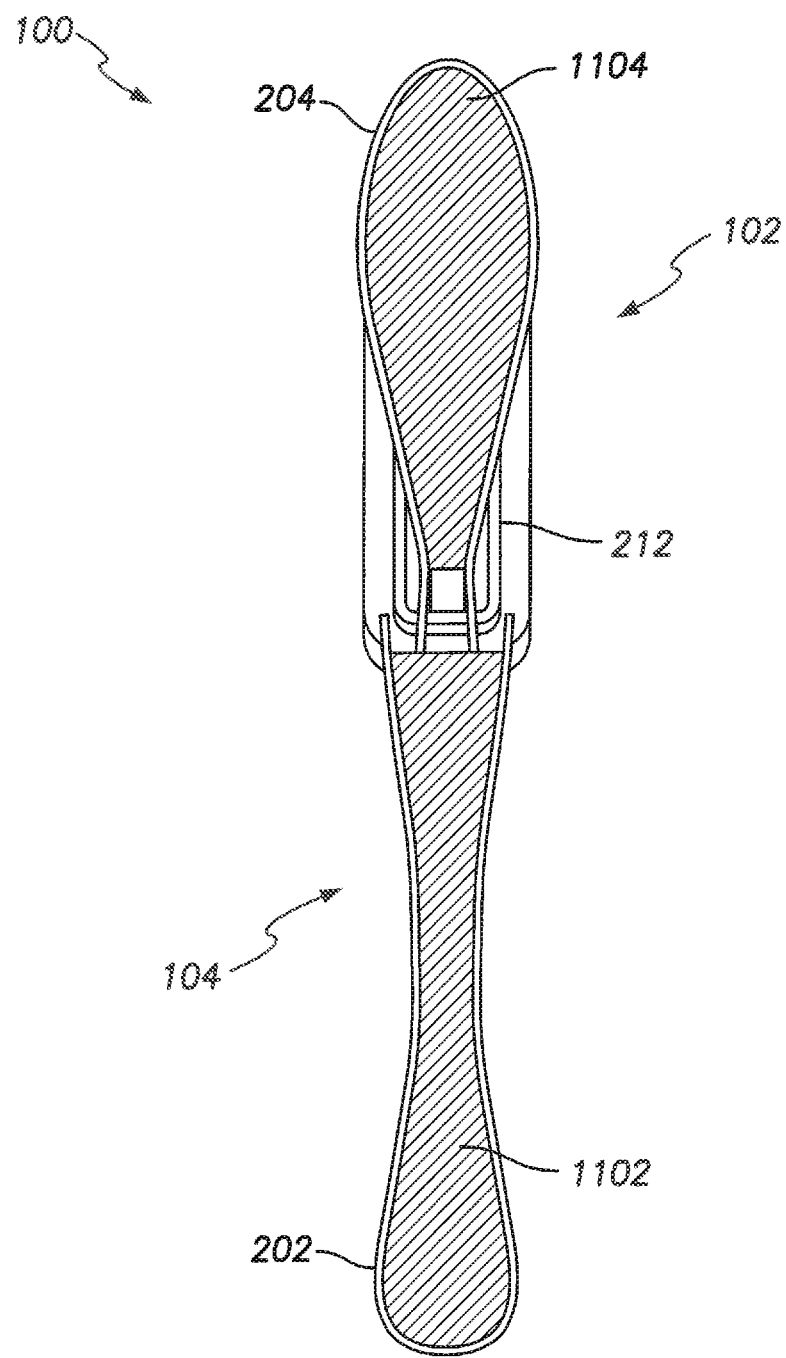
FIG. 11 is a side view of a wireless LAP sensor with the anchoring elements provided in the form of a wire frame.

FIG. 11 is a side view of a wireless LAP sensor device 100 in another additional aspect. In this aspect, the anchoring elements 202 and 204 are provided in the form of a wire frame similar to the device 100 illustrated in FIG. 5. In this aspect, an additional biocompatible material is attached to the anchoring elements 202 and 204 to form elastic webs 1102 and 1104, respectively. The elastic webs 1102 and 1104 may provide one or more of at least several enhancements to the function of the anchoring elements 202 and 204. The elastic webs 1102 and 1104 may enhance the structural integrity or elastic properties of the anchoring elements 202 and 204. The elastic webs 1102 and 1104 may increase the contact area between the anchoring elements 202 and 204 and the adjacent wall of the atrial septum 108, resulting in enhanced anchoring forces; the material forming the elastic webs 1102 and 1104 may be impregnated with active compounds such as anti-inflammatory compounds to accelerate the healing of the atrial septum and/or to encourage the overgrowth of epithelial cells and the formation of the intima in the heart of the patient. Non-limiting examples of suitable materials for the construction of the elastic webs 1102 and 1104 include: silicone rubber, polyurethane and/or any other suitable flexible biocompatible material.

vi. Additional Features of Anchoring Elements

Figure 12:
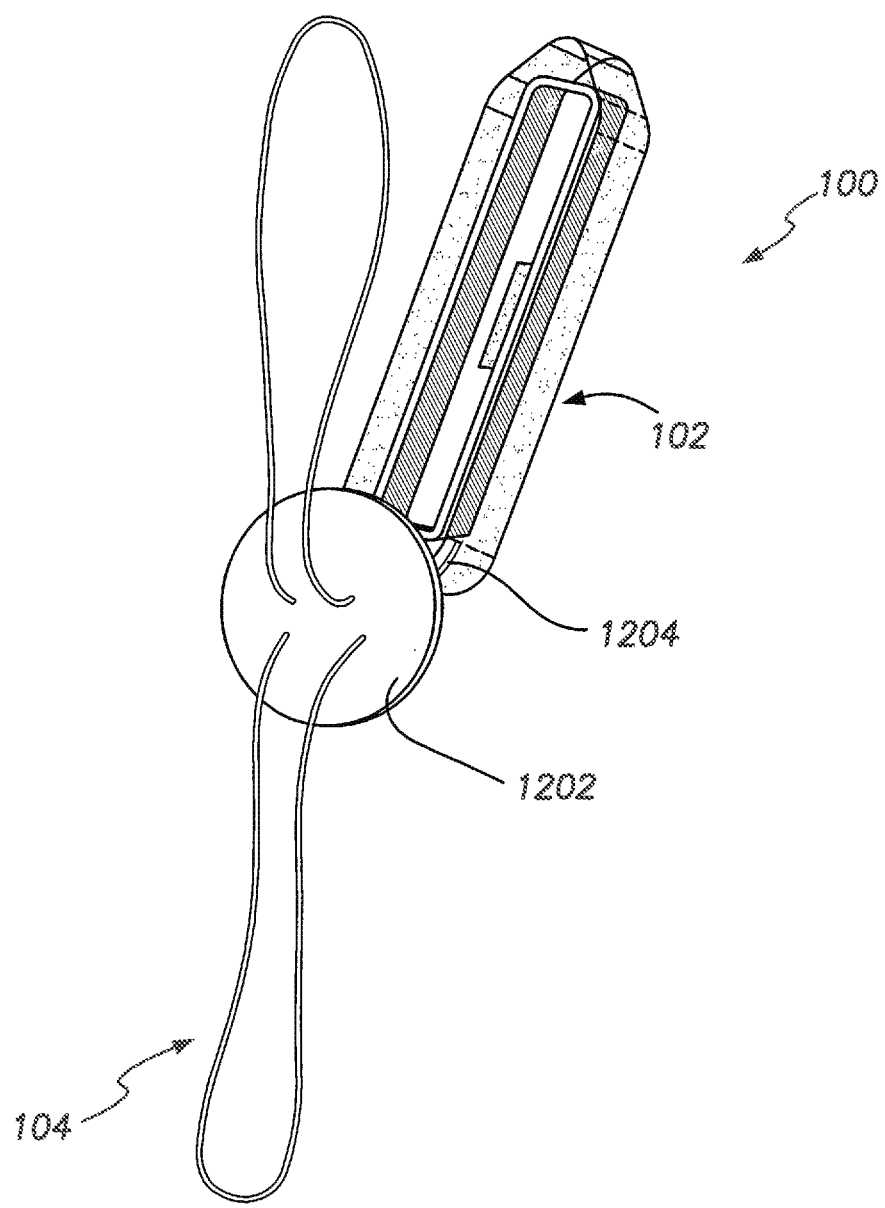
FIG. 12 is a perspective view of a wireless LAP sensor device in which a silicone disc is attached near the base of the anchoring elements.

In various embodiments, the anchoring elements 104 may incorporate additional features to enhance the function of the anchoring elements 104. FIG. 12 is a perspective view of a wireless LAP sensor device 100 in which a silicone disc 1202 is attached near the base 1204 of the anchoring elements 104 in an aspect. When the device 100 is implanted, the silicone disc 1202 is situated adjacent to the right wall of the atrial septum (not shown) along with the anchoring elements 104. The relatively large size of the silicone disc 1202 prevents the anchoring elements 104 from working through the atrial septum and instigating an embolism of the device 100 in the left atrium of the patient. Any shape of silicone disc 1202 may be used in various aspects without limitation. However, the thin disk shape provides a low profile, which may inhibit the formation and release of blood clots and may further encourage the overgrowth of epithelial cells within the right atrium to form the intima. In addition, the round shape of the silicone disc 1202 provides a reliable minimum dimension (analogous to a round manhole cover) which must pass through the atrial septum 108 to provoke an embolism of the device 100.

In an aspect, the anchoring elements 104 may include one or more radiopaque marker materials adhered to or embedded into the anchoring elements 104. Non-limiting examples of radiopaque marker materials include heavy metals such as tantalum and platinum. The marker materials may be used in conjunction with a medical visualization technology such as fluoroscopy to monitor the position of the anchoring elements 104 to determine one or more positions of the one or more anchoring elements 104 to provide positional feedback during the implantation procedure and the confirm proper deployment of the anchoring elements 104.

The marker materials may be attached at any position on the anchoring elements 104 without limitation. In one aspect, the marker materials may be attached near the free end of one or more anchoring elements 104; the distance between the one or more free ends of the anchoring elements 104 as determined from the relative positions of the free ends may be used as an additional indication of the configuration of the anchoring arms 104, and/or to confirm the deployment of the anchoring elements 104 from a folded position to an anchoring position during implantation of the device 100. In another aspect, one or more marker materials may be attached to or embedded within two or more anchor elements 104 such that the two or more anchor elements 104 may be individually identified and/or differentiated from one another using a medical visualization technology such as fluoroscopy. In this aspect, each of the two or more anchor elements 104 may be marked using a unique marker material, using a unique pattern or position, or any combination thereof.

In one illustrative example, one or more marker materials may be incorporated into a device 100 that includes a "dual propeller" arrangement of the anchoring elements 104 similar to the device illustrated in FIG. 9. In this example, the marker materials may be attached to or embedded to the anchoring elements 104 in such a way that the proximal anchoring elements 902 may be differentiated from the distal anchoring elements 904 using a medical visualization technology such as fluoroscopy. During the implantation of the device, this differentiation between the proximal anchoring elements 902 and the distal anchoring elements 904 may facilitate the proper placement of these two groups of anchoring elements 104 on opposite sides of the atrial septum.

In another additional aspect, the anchoring elements 104 may be coated with at least one surface-modifying material to impart a desired physical, chemical, or biological characteristic to the surface of the anchoring elements. In one aspect, the anchoring elements 104 may be coated with a hydrophilic coating. In this aspect, the hydrophilic coating may reduce the friction on the anchoring elements 104 to enable smooth delivery through the sheath or other catheter-based surgical instruments during implantation of the device 100. Suitable hydrophilic coating materials may also be selected to be biocompatible and non-toxic over the course of long-term and chronic residence of the device 100 in the heart of the patient. Non-limiting examples of suitable hydrophilic coating materials include: silica; silicones; other hydrophilic polymers such as polyvinyl pyrrolidone, polyethylene glycol, polyethylene oxide, polyethyloxazoline, polypropylene oxide, polyacrylamide, polyvinyl alcohol, carboxylmethyl cellulose, hydroxymethyl cellulose, hyaluronic acid and any other known biocompatible and hydrophilic coating materials.

In an additional aspect, the anchoring elements 104 may also include a medicating sleeve or may be composed of materials impregnated with active compounds. This medicating sleeve or impregnated material may contain active compounds to be introduced into the heart, applied to the septal wall or placed in the bloodstream during the implantation of the wireless LAP sensor device 100. In one aspect, the medicating sleeve or impregnated material may be silicone rubber, polyurethane or any other suitable biocompatible material impregnated with the active compound. The active compound may be provided in the form of a powder to be mixed with the biocompatible material to form a ring, sleeve or similar structure to be situated on one or more anchoring elements 104. The active compound in the medicated sleeve or impregnated material may be time released, contact released or released through any other suitable mechanism known in the art. In one aspect, the medicated sleeves or impregnated material may be impregnated with anti-inflammatory agents such as various types of steroid. In this aspect, the introduction of the anti-inflammatory agent may hasten the healing around the hole formed in the atrial septum during implantation and/or may facilitate the buildup of intima.

b. Sensor

Referring back to FIG. 2, the wireless LAP sensor device 100 includes a sensor 102 in various aspects. The sensor 102 includes a housing 206 containing a sensor circuit 210 that is connected to a deformable diaphragm 208. The sensor circuit 210 is configured to measure left atrial pressure (LAP) within the heart of a patient using capacitive pressure measurement methods and to wirelessly communicate the measured pressures to an external data acquisition device using inductive telemetry methods.

Figure 13:
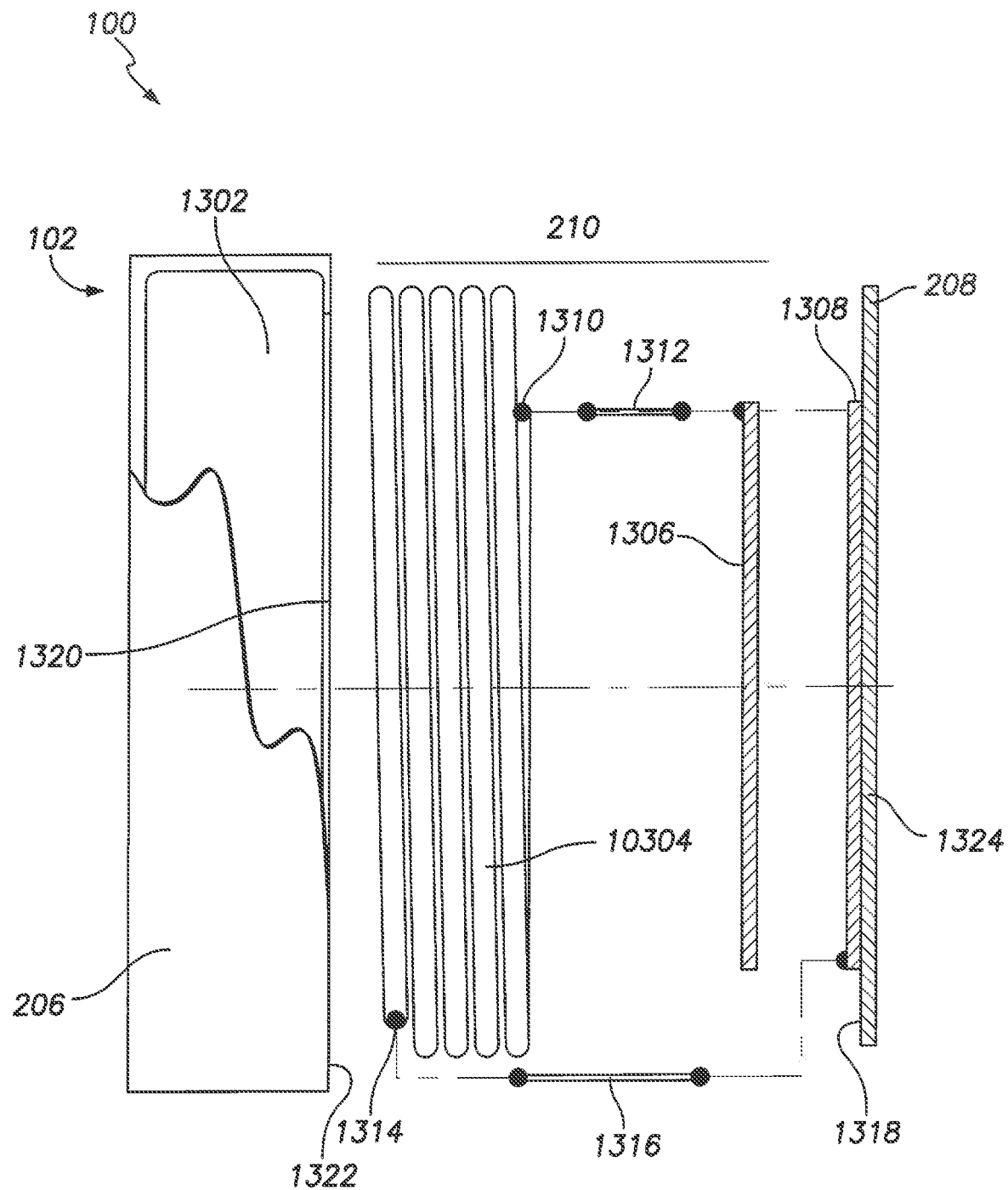
FIG. 13 is an exploded side view of the sensor with a portion of the housing removed to view the sensor's interior.

FIG. 13 is an exploded side view of the sensor 102 in one aspect with a portion of the housing 206 removed to view the housing's interior. In an aspect, the housing 206 defines a cavity 1302 within which the sensor circuit 210 is hermetically sealed beneath the diaphragm 208 to protect the sensor circuit 210 from moisture or ingress of body fluids. The sensor circuit 210 includes an inductive coil 1304, a fixed capacitor plate 1306, and a moveable capacitor plate 1308. The fixed capacitor plate 1306 is electrically connected to the inductive coil 1304 at a first end 1310 via a first lead 1312. The moveable capacitor plate 1308 is electrically connected to the inductive coil 1304 at a second end 1314 via a second lead 1316. In addition, the moveable capacitor plate 1308 is attached to an inner surface 1318 of the diaphragm 208. The sensor circuit 210 is situated within the cavity 1302 and the diaphragm 1318 is sealed over an opening 1320 formed in the upper face 1322 of the housing 206.

The fixed capacitor plate 1306 and the moveable capacitor plate 1308 together form a variable capacitor that is electrically connected in series with the inductive coil 1304 to form an LC circuit. This LC circuit intrinsically possesses a characteristic resonant frequency that may vary depending on the particular capacitance of the variable capacitor. The capacitance may vary depending on the position of the moveable capacitor plate 1308, which shifts position along with the diaphragm 208 depending on the pressure applied to the external surface 1324 of the diaphragm 208. Thus, the resonance frequency of the LC circuit formed by the components of the sensor circuit 210 may encode the left atrial pressure (LAP) when the sensor 102 is situated within the left atrium of a patient. A more detailed description of the electrical function of the sensor circuit 210, including the measurement and encoding of LAP and the wireless transmission of the measured LAP to an external data acquisition device are provided herein below.

i. Housing

The housing 206 provides a hermetically-sealed protective covering for the internal sensor circuit 210, a support surface for the moveable diaphragm 208, and in certain aspects, an anchoring surface to hold the sensor 102 fixed in place, for example as illustrated in FIG. 1. In addition, the housing 206 is designed to provide these functions with minimal interference with the operation of the diaphragm 208 and associated sensor circuit 210. Further, the housing 206 may be designed to facilitate the implantation of the wireless LAP sensor device 100, to minimize the formation and release of blood clots within the left atrium of the patient, and to enhance the adhesion of epithelial cells and associated formation of the intima within the left atrium.

In various aspects, the housing 206 may be formed from a biocompatible, non-conductive, and non-metallic material.

Non-limiting examples of suitable materials for the construction of the housing 206 include: fused silica, quartz, ceramic, and sapphire. In one aspect, the housing material may be selected to enable wireless induction/telemetry to function without any interference or shielding that a metallic housing would create; in this aspect, fused silica and quartz may be selected. In another aspect, the material may be selected for ease of fabrication. In this other aspect, the selected material may be compatible with the selected method of fabrication including, but not limited to: machining, casting, and microfabrication methods such as deposition, and any combination thereof.

The external shape of the housing 206 may be any shape capable of enclosing an internal cavity 1302 without limitation. In one aspect, the housing 206 may have a rectangular or prismatic shape, as illustrated in FIG. 1, for example. In this aspect, a rectangular or prismatic shape may potentially be easier to manufacture and may also leverage existing sensor designs and manufacturing processes known in the art. In another aspect, the housing 206 may have a cylindrical shape, as illustrated in FIG. 3, for example. In this other aspect, the cylindrical housing shape may facilitate the delivery and implantation of the wireless LAP sensor device 100 using modifications of existing catheter-based delivery methods. For example, the housing 206 may have a circular, ovoid or other rounded shape to fit through a primary lumen of a delivery catheter and to fit through a passage formed in a septal wall of the heart by a needle. In addition, the cylindrical housing shape may result in a low profile of the sensor 102 within the left atrium 106 of the patient during use. This low profile design may reduce the risk of developing or releasing blood clots and may be more amenable to the formation of the intima during an extended and chronic residence of the device 100 within the heart of the patient.

ii. Diaphragm

Figure 14:
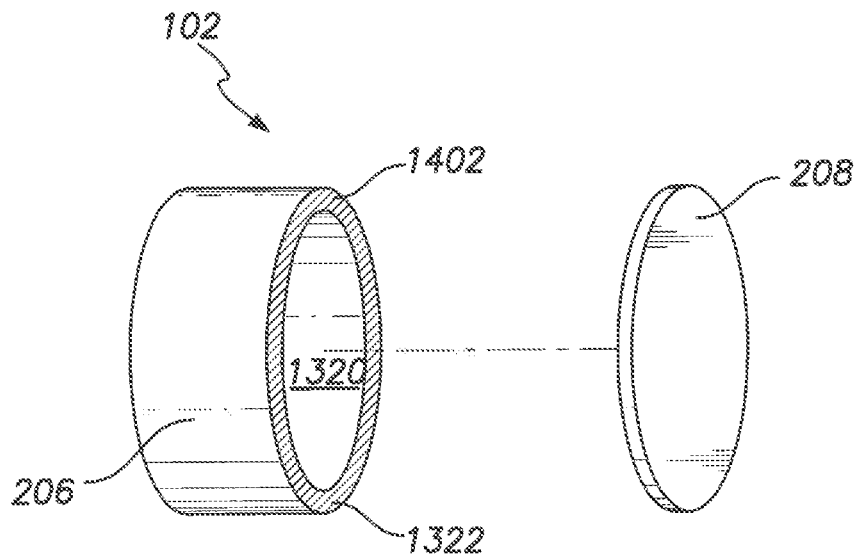
FIG. 14 is an exploded diagram illustrating one technique for attaching the flexible diaphragm to the housing.
Figure 15:
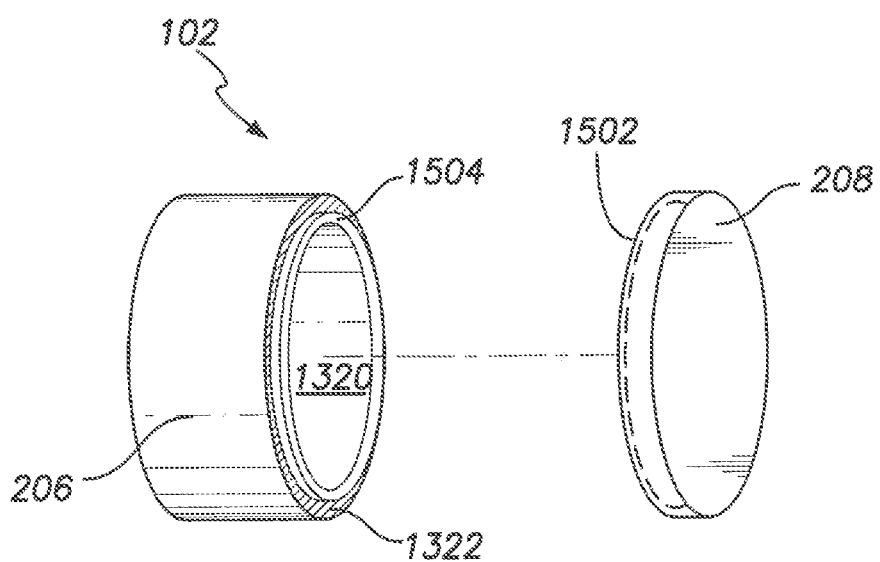
FIG. 15 is an exploded diagram illustrating another technique for attaching the flexible diaphragm to the housing.

Referring back to FIG. 13, the sensor 102 includes a flexible diaphragm 208 coupled to the sensor circuit 210. The diaphragm 208 may be sealed over an opening 1320 formed in the upper face 1322 of the housing 206 to form the hermetically-sealed cavity 1302 containing the sensor circuit 210. FIG. 14 is an exploded diagram illustrating one technique for attaching the flexible diaphragm 208 to the housing 206 in one aspect. In this aspect, the diaphragm 208 may be provided in the form of a thin disk that is sealed around the circumference of a support surface 1402 provided on the upper face 1322 of the housing 206. FIG. 15 is an exploded diagram illustrating another technique for attaching the flexible diaphragm 208 to the housing 206 in another aspect. In this other aspect, the diaphragm 208 may be formed with a lip 1502 that is placed over the seat 1504 provided on the upper face 1322 of the housing 206. Thus, an inside surface of the lip 1502 may, for example, be adhered to an outside surface of the seat 1504. The diaphragm 208 may be attached to the housing 206 using a variety of techniques including, but not limited to laser welding and adhesive attachment (e.g., using an epoxy).

In use, the diaphragm 208 deflects in response to the net force resulting from differences in the pressure inside and outside the housing 206. The pressure outside the housing 206 may be the left atrial pressure (LAP) when the sensor 102 is situated within the left atrium of the patient. Depending on the condition of the patient, LAP may range from about 0.01 mm Hg to about 100 mm Hg. Without being limited to any particular theory, the mean LAP in a healthy patient may be about 12 mm Hg, and the peak LAP in patients with various heart conditions may range from about 10 mm Hg to about 60 mm Hg or higher, depending on the particular type of heart condition and the severity of the heart condition.

In various aspects, the pressure inside the housing 206 may range from about 0.01 mm Hg to about 100 mm Hg. Pressure, as used herein, refers to the gage pressure in a system, defined as the pressure above or below atmospheric pressure; the atmosphere has a gage pressure of about 0 mm Hg by this definition. Without being limited to any particular theory, the sensitivity of the diaphragm 208 to relatively small changes in LAP may be enhanced by matching the pressures inside and outside of the housing 206. If pressure inside the housing 206 is equal to the mean LAP and the sensor 102 is situated in the left atrium of the patient, no net force would be exerted in the diaphragm 208 when the LAP was equal to the mean LAP. In this situation, small changes in LAP above or below the mean LAP would exert relatively small net forces on the diaphragm 208. As a result, a relatively thin diaphragm 208 may be used due to the relatively low range of anticipated forces acting on the diaphragm 208. In addition, the diaphragm 208 may undergo a smaller range of deflections in this situation, allowing the diaphragm 208 to operate well within the linear elastic region of the material from which the diaphragm is constructed. The pressure inside the housing 206 may be achieved by sealing the diaphragm 208 to the housing 206 under pressure conditions matched to the desired pressure inside the housing.

In another aspect, the gage pressure inside the housing may be equal to about 0 mm Hg if the diaphragm 208 is sealed to the housing 206 under atmospheric conditions. In this aspect, the diaphragm 208 may deflect inwards when situated within the left atrium and when exposed to LAP levels in excess of 0 mm Hg. As a result, the range of forces anticipated to act on the diaphragm 208, and the anticipated range of deflections of the diaphragm 208 may be higher than if the pressure inside the housing 206 was more closely matched to the mean LAP.

In various aspects, the diaphragm 208 may be a precision micromachined structure that may undergo a deflection during use ranging from about 1 nanometer to about 100 micrometers in order to provide a frequency response suitable for the measurement of the hemodynamic parameters associated with regular as well as irregular heartbeats. The diaphragm 208 may be constructed using any suitable biocompatible and elastic material. Non-limiting examples of materials suitable for the construction of the diaphragm include: silica, silicon, quartz, titanium, stainless steel, MP35N and any other known suitable material. In one aspect, the diaphragm 208 may be micromachined from fused silica or fused quartz.

Referring back to FIG. 13, the movable capacitor plate 1308 may be attached to the inner surface 1318 of the diaphragm 208. In one aspect, an insulating layer of epoxy of other coating may be laid down on the inner surface 1318 of the diaphragm 208 and the moveable capacitor plate 1308 may be attached using the epoxy adhesive. In this aspect, deflections of the diaphragm 208 alter the separation distance between the moveable capacitor plate 1308 and the fixed capacitor plate 1306, inducing a corresponding shift in the resonance frequency of the sensor circuit 210. In this aspect, the diaphragm 208 may be constructed from a non-conductive material such as fused silica or fused quartz to minimize the electrical interference of the diaphragm 208 with the function of the sensor circuit 210.

In another aspect, the diaphragm 208 may be formed from an electrically conductive material. Non-limiting examples of suitable electrically conductive materials include: metals such as titanium; and doped silicon materials, such as highly doped SiB or SiGeB. In this other aspect, the conductive diaphragm 208 may function as the moveable capacitor plate 1308, obviating the need to attach a dedicated moveable capacitor plate 1308 to the diaphragm 208. Due to the elimination of the dedicated moveable capacitor plate 1308 and associated adhesive, the diaphragm 208 may be more sensitive to changes in pressure in this aspect compared to a diaphragm 208 with an attached moveable capacitor plate 1308 as described previously herein.

iii. Sensor Circuit

Figure 16A:
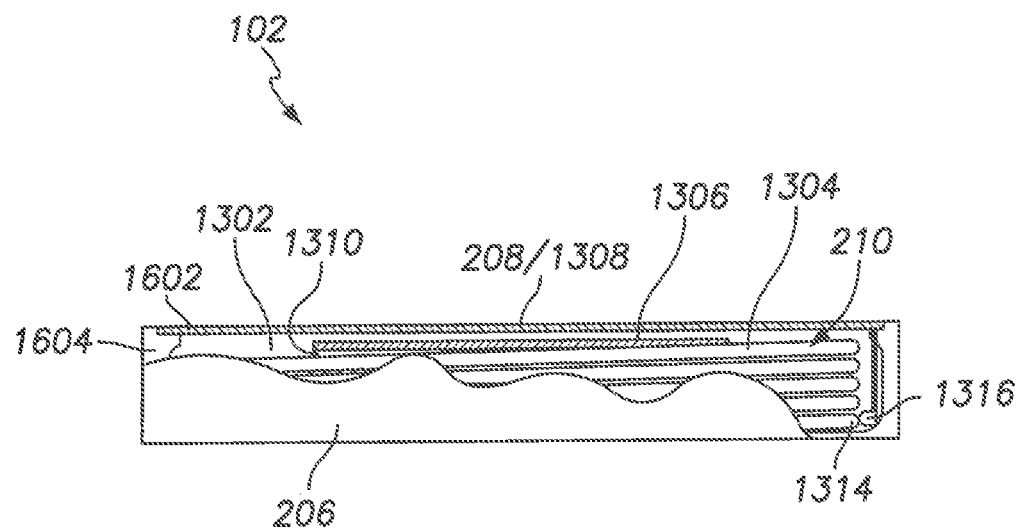
FIG. 16A is a cutaway side view and FIG. 16B is a cutaway top view of a sensor illustrating the relationship of the various components of the sensor circuit.
Figure 16B:
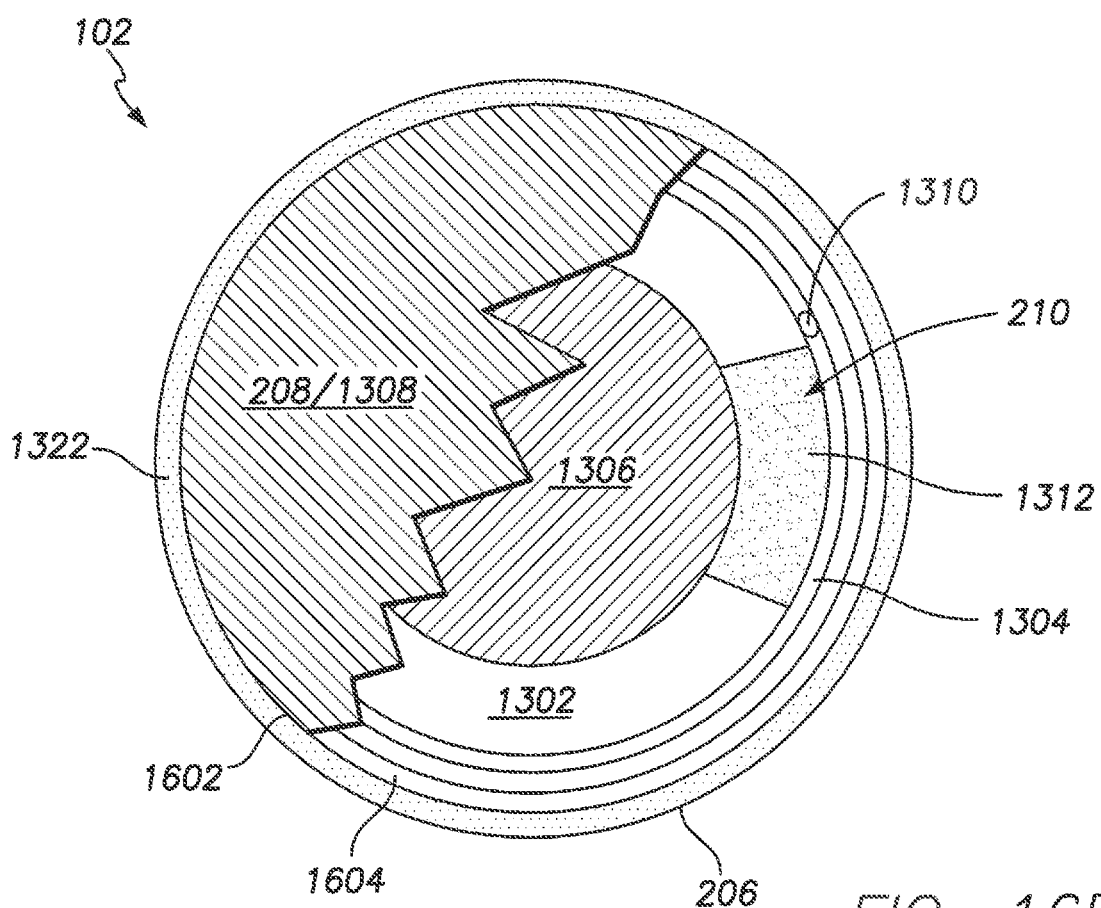

Referring back to FIG. 13, the sensor 102 includes a sensor circuit 210 electrically attached to the diaphragm 208 and sealed within the cavity 1302 formed within the housing 206 in various aspects. FIG. 16A is a cutaway side view and FIG. 16B is a cutaway top view of a sensor 102 illustrating the relationship of the various components of the sensor circuit 102 in one aspect. The sensor circuit 210 includes an inductive coil 1304 electrically connected in series to a variable capacitor made up of a fixed capacitor plate 1306 and a moveable capacitor plate 1308. The fixed capacitor plate 1306 is electrically connected to the inductive coil 1304 at a first end 1310 via a first lead 1312. In this aspect, the first lead 1312 may provide at least some structural support to hold the fixed capacitor plate 1306 in a stationary position within the housing 206. The diaphragm 208 in this aspect is constructed of a thin disk of a conductive material such as titanium and functions as the moveable capacitor plate 1308 as described previously herein. The diaphragm 208 is electrically connected to a second end 1314 of the inductive coil 1304 via a second lead 1316. An outer edge 1602 of the diaphragm 208 may be sealed to a circumferential step 1604 formed in the in the upper face 1322 of the housing 206. The diaphragm 208 sealed to the upper face 1322 of the housing 206 define the cavity 1302 containing the sensor circuit 210

Figure 17:
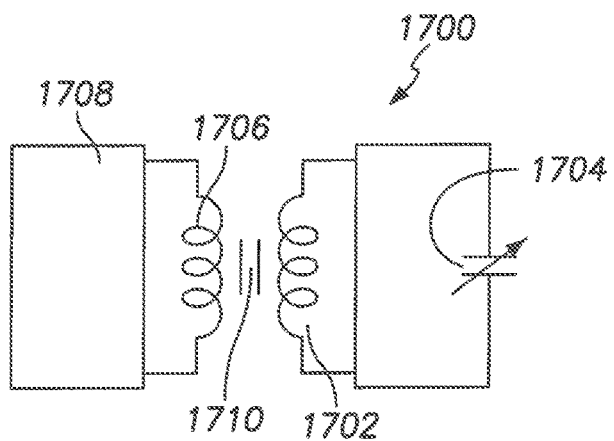
FIG. 17 is a schematic diagram illustrating an idealized resonant sensor circuit.

The sensor circuit 210 measures left atrial pressure using capacitive pressure measurement methods. The inductive coil 1304, fixed capacitor plate 1306, and moveable capacitor plate 1308 are electrically connected in series to form a resonant circuit. FIG. 17 is a schematic diagram illustrating an idealized resonant sensor circuit 1700. The resonant sensor circuit 1700 includes the inductor coil 1702 with an inductance $L_s$ in series with a variable capacitor 1704 with a capacitance $C_s$. Without being limited to any particular theory, the resonant frequency f of this resonant sensor circuit 1700 may be expressed in terms of $L_s$ and $C_s$ according to Eqn. I:

$$f = \frac{1}{2\pi\sqrt{L_s C_s}} \qquad \text{Eqn. (I)}$$

The capacitance $C_s$ of the resonant sensor circuit 1700 is influenced by the separation distance of the moveable capacitor plate 1308 from the fixed capacitor plate 1306 of the sensor 102. This separation distance may change as a result of the deflection of the diaphragm 208 in response to changes in the left atrial pressure (LAP).

The resonant frequency f of the resonant sensor circuit 1700 may be obtained using inductive telemetry methods. Referring again to FIG. 17, a data acquisition device 1708 that includes an external antenna coil 1706 may be used to perform the inductive telemetry in one aspect. The data acquisition device 1708 may communicate with the resonant sensor circuit 1700 via a magnetic coupling 1710 of the external antenna coil 1706 with the induction coil 1702 of the resonant sensor circuit 1700. This magnetic coupling 1710 inductively transfers power from the data acquisition device 1708 to the resonant sensor circuit 1700. This transferred power energizes the resonant sensor circuit 1700, which reflects back a load impedance to the acquisition device 1708 in response. Using electrical engineering methods well-known in the art, the resonant frequency f of the resonant sensor circuit 1700, and by extension the LAP, may be determined. In one aspect, the magnitude of the reflected impedance from the sensor circuit 1700 may be used to determine the resonant frequency f. In another aspect, the phase of the reflected impedance may be used to determine the resonant frequency f. In an additional aspect, spectral analysis of the reflected impedance may be performed to determine the resonant frequency f of the resonant sensor circuit 1700.

The range of resonant frequencies f may be influenced by the particular values of the sensor's inductance $L_s$ and capacitance $C_s$. The particular values of $L_s$ and $C_s$ incorporated into the resonant sensor circuit 1700 may be determined using standard electrical engineering principals. For example, $L_s$ may be influenced by the number of coils and coil dimensions in the inductive coil 1304. In another example, the capacitance $C_s$ may be influenced by the size, shape, separation distance, and materials used in the construction of the fixed and moveable capacitor plates, as well as the stiffness and surface area of the diaphragm.

iv. Additional Sensor Features

In an aspect, the sensor 102 may include one or more radiopaque marker materials adhered to or embedded into the sensor 102. Non-limiting examples of suitable radiopaque marker materials include heavy metals such as tantalum and platinum. The marker materials may be used in conjunction with a medical visualization technology such as fluoroscopy to monitor the position of the sensor 102 and/or to provide positional feedback during the implantation procedure. The marker materials may be attached at any position on the sensor 102 without limitation.

Figure 18A:
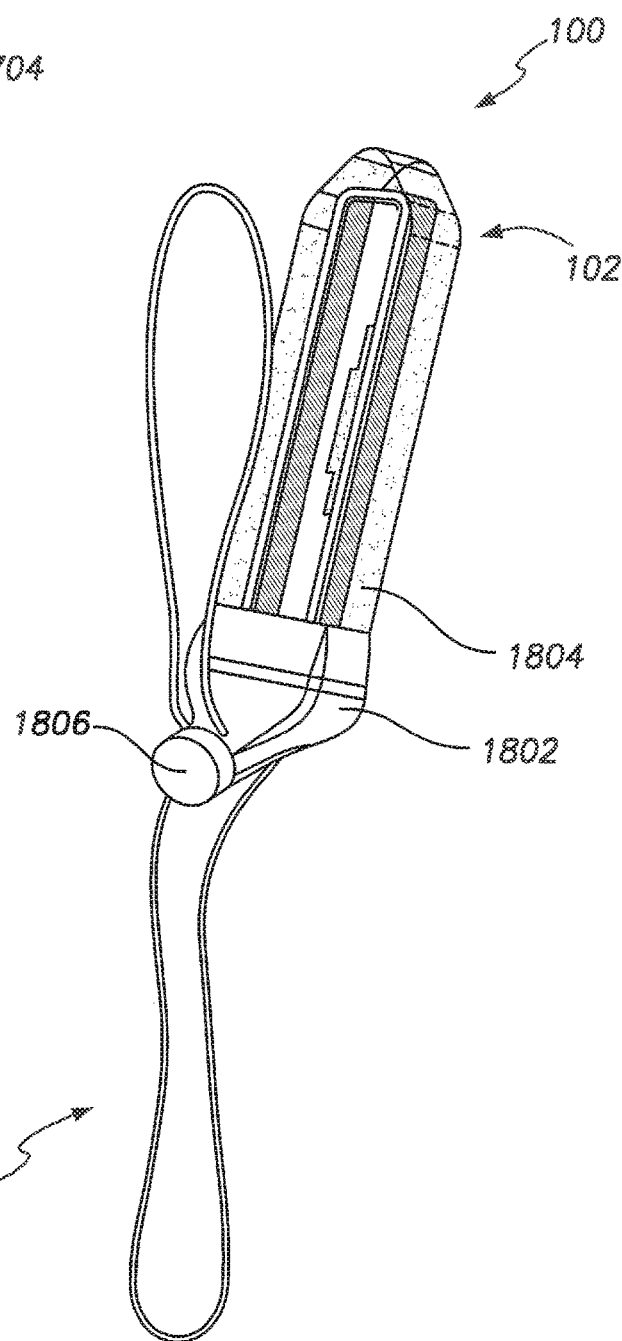
FIG. 18A is a perspective view and FIG. 18B is a side view of a sleeve mounted on a proximal end of the sensor.
Figure 18B:
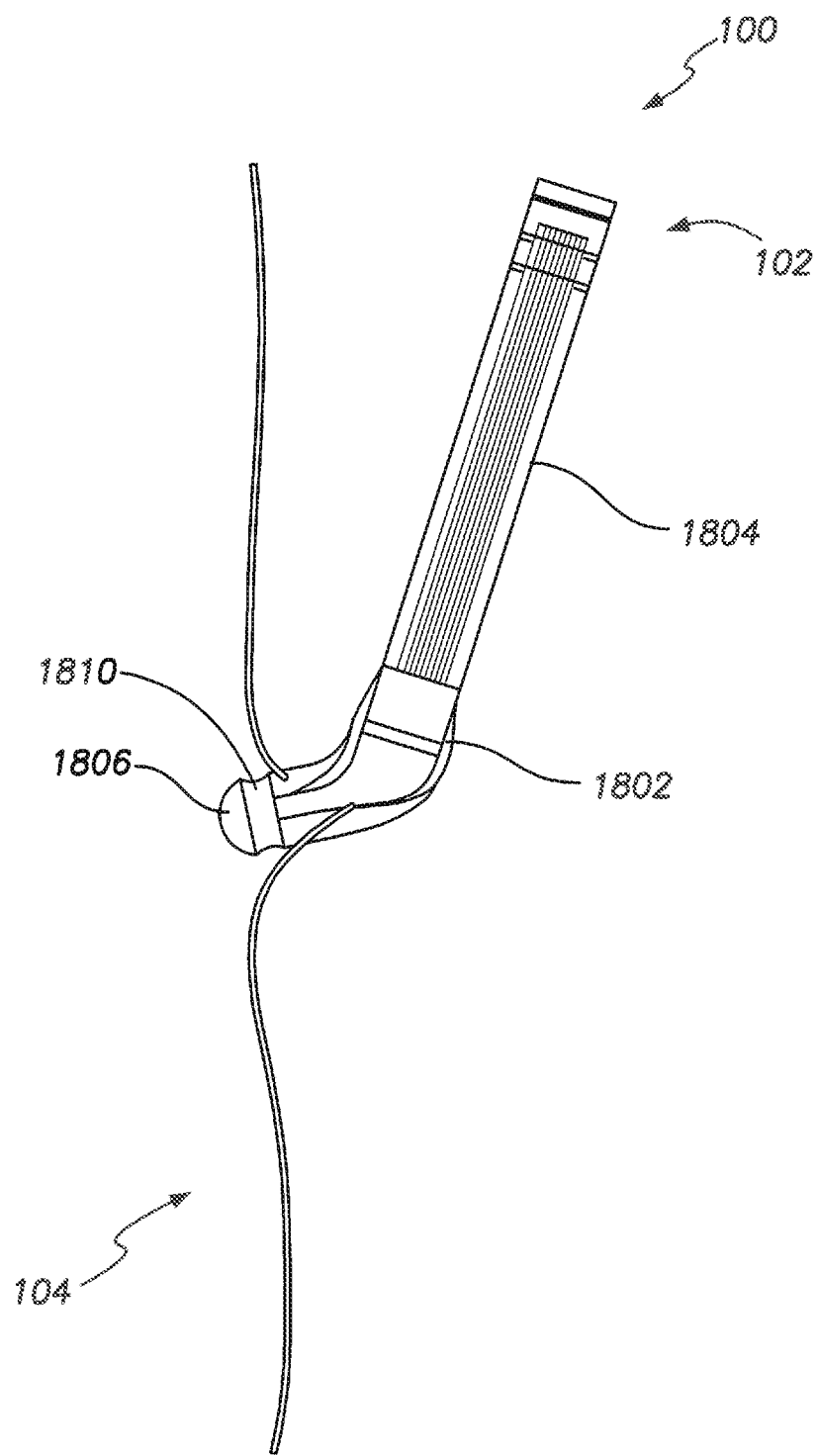

In one aspect, the sensor 102 may also include a sleeve constructed of a biocompatible material including, but not limited to silicone. FIG. 18A is a perspective view and FIG. 18B is a side view of a sleeve 1802 mounted on a proximal end 1804 of the sensor 102. The sleeve 1802 may be shaped to fit snugly over the proximal end 1804 of the sensor 102 and may further cover the one or more anchoring elements 104 at each element's point of attachment to the sensor 102.

In this aspect, the sleeve 1802 may facilitate the insertion of the sensor 102 into the left atrium of the patient. The material of the sleeve 1802 may smooth potentially discontinuous transitions such as the joining of the attached ends of the anchoring elements 104 to the proximal end 1804 of the sensor 102. In addition, the sleeve 1802 may be coated and/or impregnated with any one or more materials to facilitate the insertion of the sensor 102 and to enhance the biocompatibility of the sensor during chronic residence in the left atrium of the patient. Non-limiting examples of materials suitable for incorporation into the material of the sleeve 1802 include: one or more radiopaque marker materials described herein previously to provide positional feedback during implantation and/or retrieval; hydrophilic coatings to reduce the friction of the sensor 102 during deposition and/or retrieval; active compounds to reduce inflammation, inhibit the formation and release of blood clots, and to facilitate the adhesion of epithelial cells and associated formation of the intima within the left atrium of the patient, and any combination thereof.

The sleeve 1802 may further include a knob 1806 projecting away from the proximal end 1804 along an axis of symmetry 1808 of the one or more anchoring elements 104 to facilitate the snagging and/or retrieval of the sensor 102 from the patient. The knob 1806 may include a reduced diameter neck 1810 or circumferentially extending groove that may provide a region to which a tether may be attached during implantation and/or retrieval of the sensor 102.

Figure 19A:
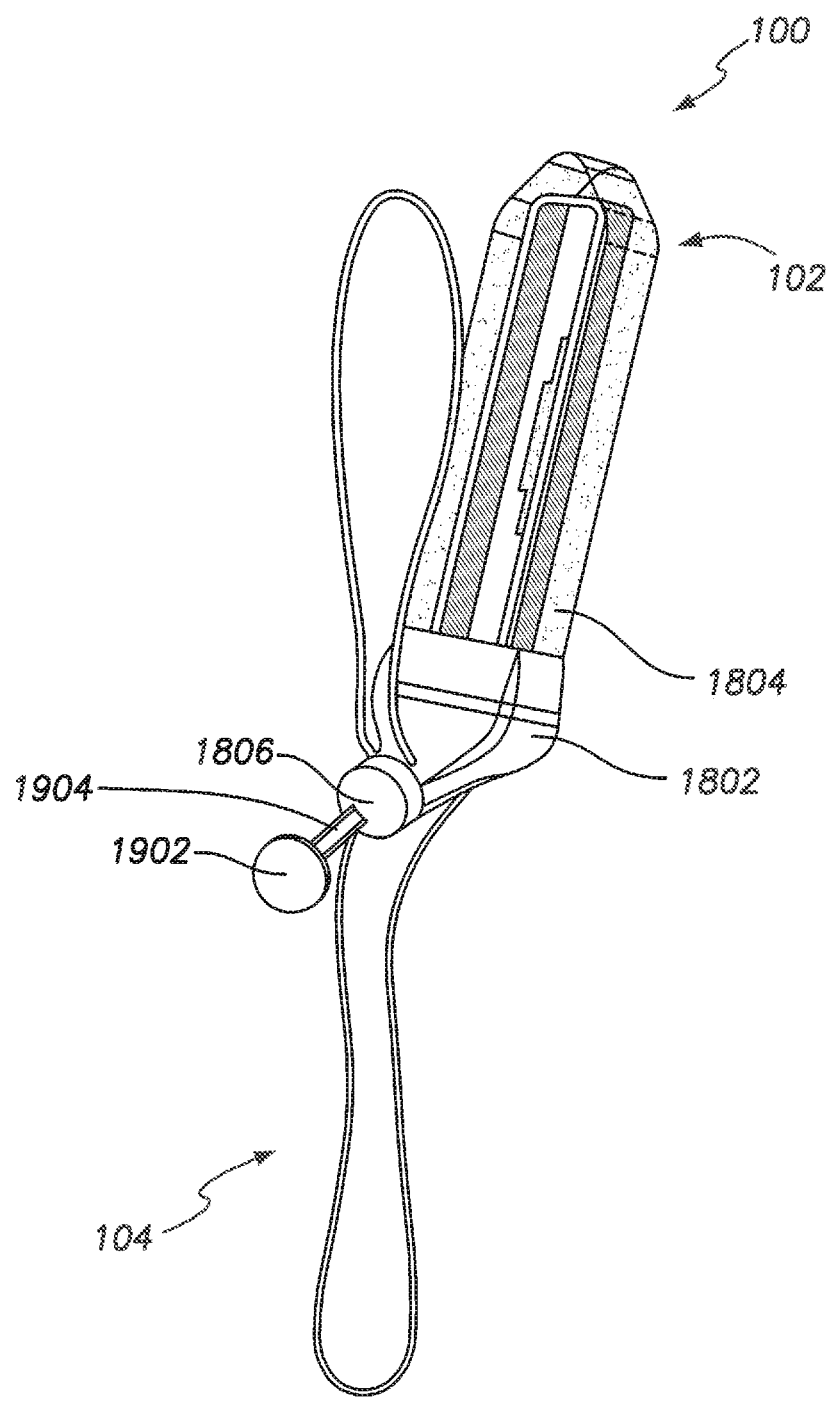
FIG. 19A is a perspective view and FIG. 19B is a side view of a sleeve in another aspect that further includes an extension plug extending along the axis of symmetry of the anchoring elements to further facilitate the snagging and/or retrieval of the sensor from the patient.
Figure 19B:
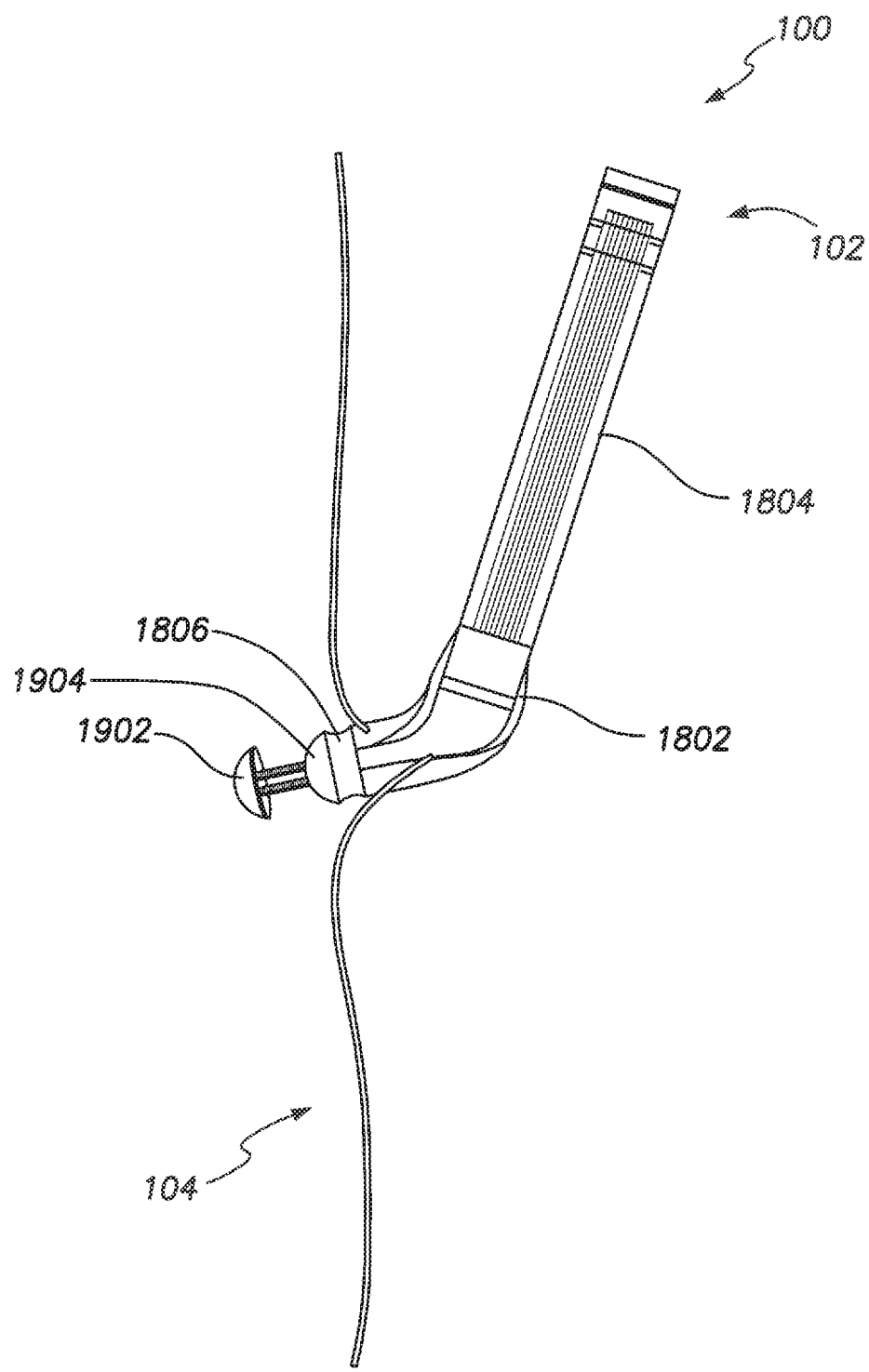

FIG. 19A is a perspective view and FIG. 19A is a side view of a sleeve 1802 in another aspect that further includes an extension plug 1902 extending along the axis of symmetry 1808 of the one or more anchoring elements 104 to further facilitate the snagging and/or retrieval of the sensor 102 from the patient. In this other aspect, the extension plug 1902 may be attached to the knob 1806 by a flexible lanyard 1904 to facilitate the snagging of the extension plug 1902 by a tether during the implantation and/or retrieval of the sensor 102.

In the various aspects described herein above, the sleeve 1802 may be coated and/or impregnated with an active compound. This medicating sleeve or impregnated material may contain active compounds to be introduced into the heart, applied to the septal wall or placed in the bloodstream during the implantation of the wireless LAP sensor device 100. In one aspect, the medicating sleeve or impregnated material may be silicone rubber, polyurethane or any other suitable biocompatible material impregnated with the active compound. The active compound may be provided in the form of a powder to be mixed with the biocompatible material to form the sleeve 1802. The active compound in the medicated sleeve or impregnated material may be time released, contact released or released through any other suitable mechanism known in the art. In one aspect, the medicated sleeves or impregnated material may be impregnated with anti-inflammatory agents such as various types of steroid. In this aspect, the introduction of the anti-inflammatory agent may hasten the healing around the hole formed in the atrial septum during implantation and/or may facilitate the buildup of intima.

In other aspects, the sensor 102 may further include one or more bioactive coatings to enhance the biocompatibility and function of the sensor 102 during extended chronic implantation in the left atrium of the patient. The sensor may include a coating that includes a bioactive compound to discourage excessive tissue overgrowth or thrombus formation. The diaphragm 208 may include a coating to encourage the adhesion of epithelial cells and the formation of the intima.

In another additional aspect, the sensor 102 and/or sleeve 1802 may be coated with at least one surface-modifying material to impart a desired physical or chemical characteristic to the surface of the sensor 102. In one aspect, the sensor 102 may be coated with a hydrophilic coating. In this aspect, the hydrophilic coating may reduce the friction on the sensor 102 to enable smooth delivery through the sheath or other catheter-based surgical instruments during implantation and/or retrieval of the device 100. Suitable hydrophilic coating materials may also be selected to be biocompatible and non-toxic over the course of long-term and chronic residence of the device 100 in the heart of the patient. Non-limiting examples of suitable hydrophilic coating materials include: silica; silicones; other hydrophilic polymers such as polyvinyl pyrrolidone, polyethylene glycol, polyethylene oxide, polyethyloxazoline, polypropylene oxide, polyacrylamide, polyvinyl alcohol, carboxylmethyl cellulose, hydroxymethyl cellulose, hyaluronic acid, and any other known biocompatible and hydrophilic coating materials II. Methods of Using Wireless LAP Sensor In various aspects, the wireless LAP sensor device 100 may be implanted and/or retrieved using modifications of catheter-based surgical methods as performed by the elements of a delivery/retrieval system. The delivery/retrieval system and implantation/retrieval methods in these various aspects ensure the fail-safe delivery of the device 100 and provide for repositioning and/or extraction of chronic implants.

Figure 20:
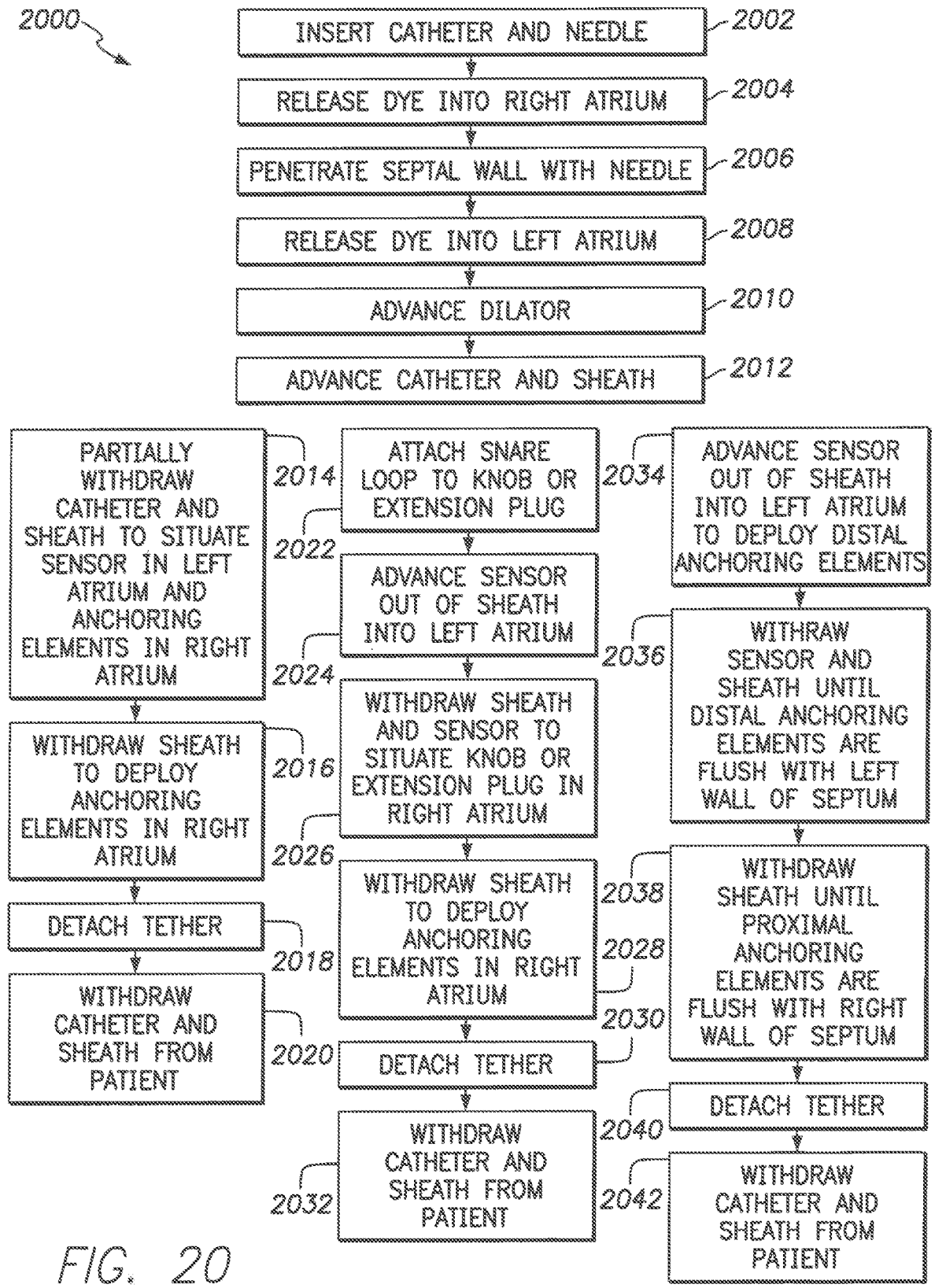
FIG. 20 is a flow chart illustrating a method of implanting a wireless LAP sensor device in various aspects.

FIG. 20 is a flow chart illustrating a method 2000 of implanting the wireless LAP sensor device 100 in an aspect. The method 2000 includes a set of initial steps common to the implantation of all devices 100, and at least two sets of specialized final steps to complete the implantation of the device 100, taking into account the configuration and locations of the anchoring elements 104 relative to the atrial septum of the patient.

Figure 21A:
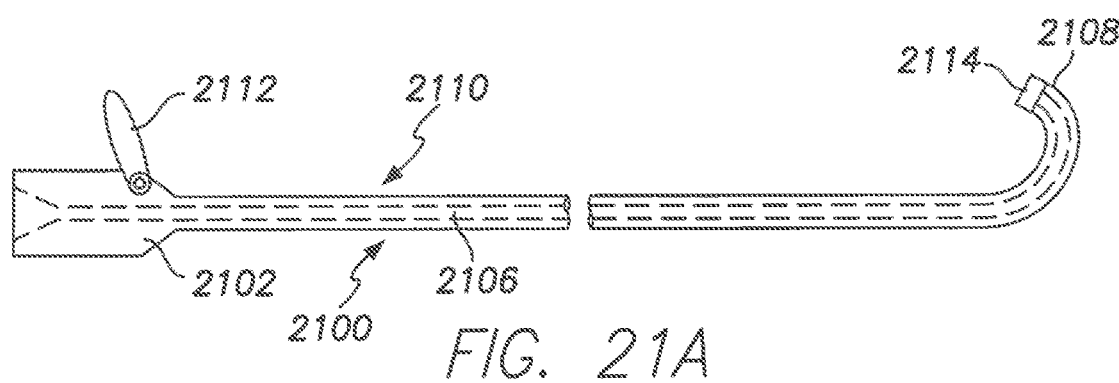
FIG. 21A is a side view of a catheter used to implant a wireless LAP sensor device.
Figure 21B:
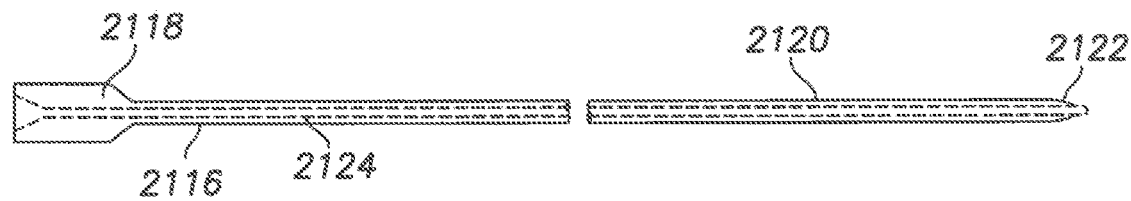
FIG. 21B is a side view of a dilator used to implant a wireless LAP sensor device.
Figure 21C:
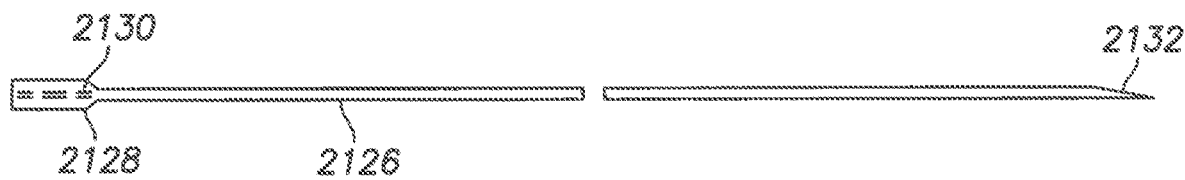
FIG. 21C is a side view of a needle used to implant a wireless LAP sensor device.

Side views of several components of a delivery/retrieval system are illustrated in FIGS. 21A-C. FIG. 21A is a diagram of one aspect of an introducer catheter 2100 or sheath. In this one aspect, the introducer catheter 2100 may have a proximal end with a housing 2102. The catheter 2100 may be formed of polyether block amide, high density polyethylene, silicone rubber, polyurethane or other materials. The materials used to form the catheter 2100 may be biocompatible to prevent complication during insertion procedures.

In one aspect, the housing 2102 may be formed to couple to other devices or components. For example, the housing 2102 may be formed to receive a dilator, needle or similar component. The proximal end of the catheter 2100 may also include openings to a set of lumens 2106 within the catheter 2100. As used herein "set" refers to any number of items including one. The catheter 2100 may contain any number of lumens. The lumens may run the length of the catheter or only run over a portion of the catheter 2100. The lumens may include a primary lumen 2106. The catheter 2100 may have a diameter large enough to allow insertion of other components such as a dilator, needles and leads. The diameter may be small enough to enter and traverse the vascular system of a patient. In one embodiment, the diameter of the catheter 2100 may be 1-10 mm. The primary lumen 2106 may have a diameter sufficient to receive a lead, dilator, needle or other components.

In one aspect, the catheter 2100 may be a deflectable catheter. The catheter 2100 may be manipulated to curve at its distal end 2108 to facilitate insertion. In a further embodiment, the catheter may be precurved. The catheter 2100 may include a main body 2110. The main body 2110 may have any length. In one embodiment, the main body 2110 has sufficient length to traverse an intravenous path to the right atrium of a heart. The housing 2102 may include a mechanism 2112 to control the distal end 2108 of the catheter 2110 as it is advanced into a patient. The mechanism 2112 may be a lever as illustrated in FIG. 21A, a control stick, a handle or other mechanism to control the curve of the distal end 2108 of the catheter 2100 using a wire line system or similar system. The distal end 2108 may contain or be covered with a marker 2114 to assist in the insertion process. The marker 2114 may be a heavy metal such as tantalum or similar substance that is visible via fluoroscopy or other system for tracking instruments in a patient, similar to the radiopaque markers described previously herein above.

FIG. 21B is a diagram of one aspect of a dilator 2116. The dilator 2116 may have a housing 2118 at the proximal end, a long tubular body 2120 and a distal tip 2122. The long tubular body 2120 may define an inner lumen 2124. The inner lumen 2124 and body 2120 may be flexible to assist during insertion of the dilator 2116. The dilator 2116 may be formed from silicon rubber, polyurethane, polyether block amide, high density polyethylene and other materials. The diameter of the dilator 2116 may be between 1-8 mm. In one embodiment, a portion of the dilator 2116 near the distal tip 2112 may have a larger outer diameter. In one embodiment, the length of this enlarged portion may be 5-8 mm. The length of a typical distal end may be 1-5 mm.

FIG. 21C is a diagram of one aspect of a needle 2126. The needle 2126 may have a proximal end 2128 with an enlarged diameter. The proximal end 2128 may be formed to be coupled to other instruments and devices. For example, the proximal end 2128 may be coupled to a dye injection device or similar device. The proximal end 2128 may also include an opening to an interior lumen 2130 or set of lumens. These lumens may run the entire length of the needle 2126 or over a portion of the needle 2126. The needle 2126 may be formed from a flexible material to allow it to follow the path of a dilator 2116 or catheter 2100 through a vascular system of a patient to the heart. In one embodiment, the needle 2126 may be partially or fully formed from steel, Nitinol (an alloy of nickel and titanium), or another alloy or metal. The needle 2120 may have a diameter of 0.25 to 3 mm or any other suitable diameter.

In one aspect, the distal end of the needle 2120 may form a point 2132. The point 2132 may be sufficiently sharp to puncture through organic structures. The end point 2132 may also be open allowing access to the interior lumen 2130. In another embodiment, the needle 2126 may be solid with a solid tip 2132.

Referring back to FIG. 20, the method 2000 of implanting the wireless LAP sensor device 100 includes inserting a catheter and needle at step 2002 to advance the needle into the right atrium of the patient and releasing a dye into the right atrium at step 2004 to confirm proper placement of the catheter. The dye may be used in connection with fluoroscopy or similar techniques and systems for monitoring instrument position in the body of a patient. The distal end of the catheter may be positioned adjacent to the atrial septum and the fossa ovalis. The needle then penetrates the atrial septum at step 2006 and dye is released into the left atrium at step 2008 to confirm proper placement of the catheter. The release of dye or other markers may continue through the process of penetration or may be restarted just after penetration of the septal wall. The dilator is then advanced through the hole formed in the atrial septum at step 2010 to enlarge the hole formed by the needle, followed by advancement of the catheter and sheath through the enlarged hole at step 2012.

Once the catheter and sheath have been advanced through the atrial septum at step 2012, the remaining steps of the method 2000 performed to situate and anchor the wireless LAP sensor device 100 may differ depending on the particular design of the device. In one aspect, the remaining steps may depend on whether the device 100 includes anchoring elements situated adjacent to the right wall of the atrial septum, as illustrated for example in FIG. 1, or whether the device 100 includes anchoring elements situated adjacent to both the left and right walls of the atrial septum, as illustrated for example in FIG. 3.

Figure 22A:
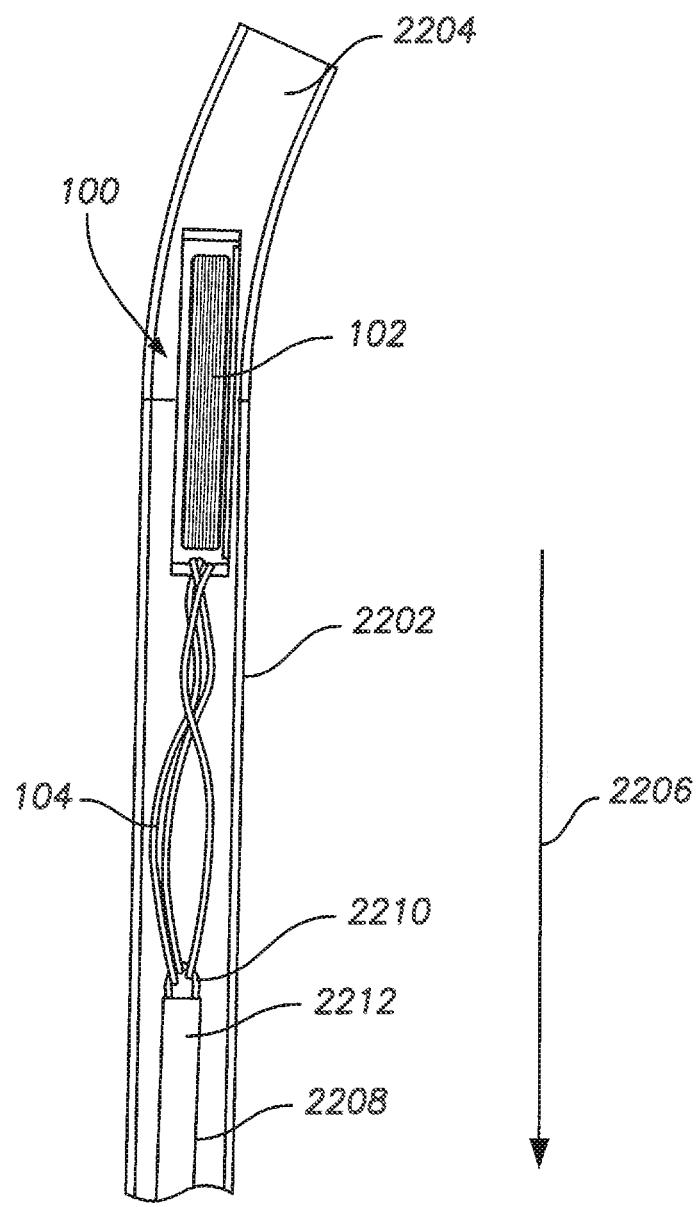
FIGS. 22A-D are side views of a wireless LAP sensor device and a sheath for the delivery thereof, the device being illustrated at various steps in the course of being implanted.
Figure 22B:
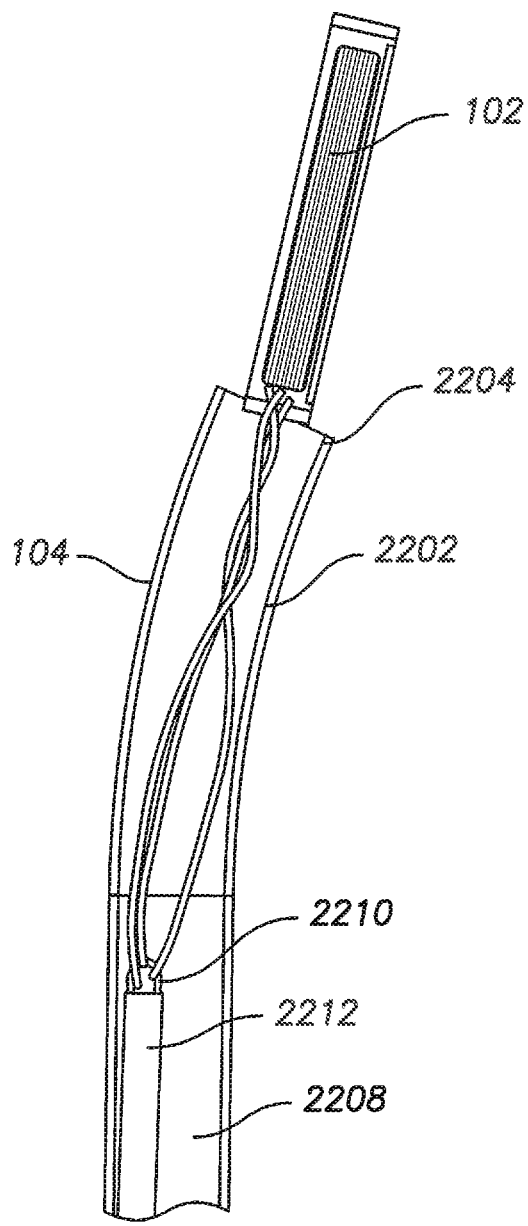
Figure 22C:
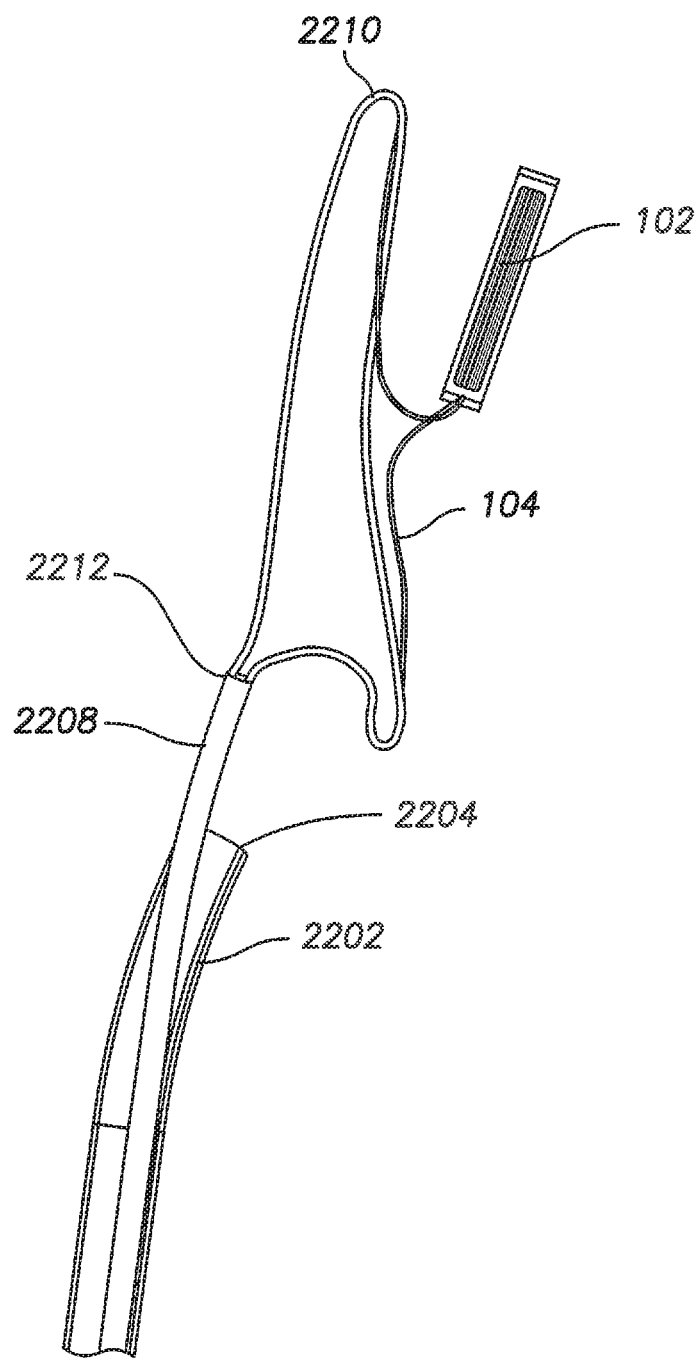
Figure 22D:
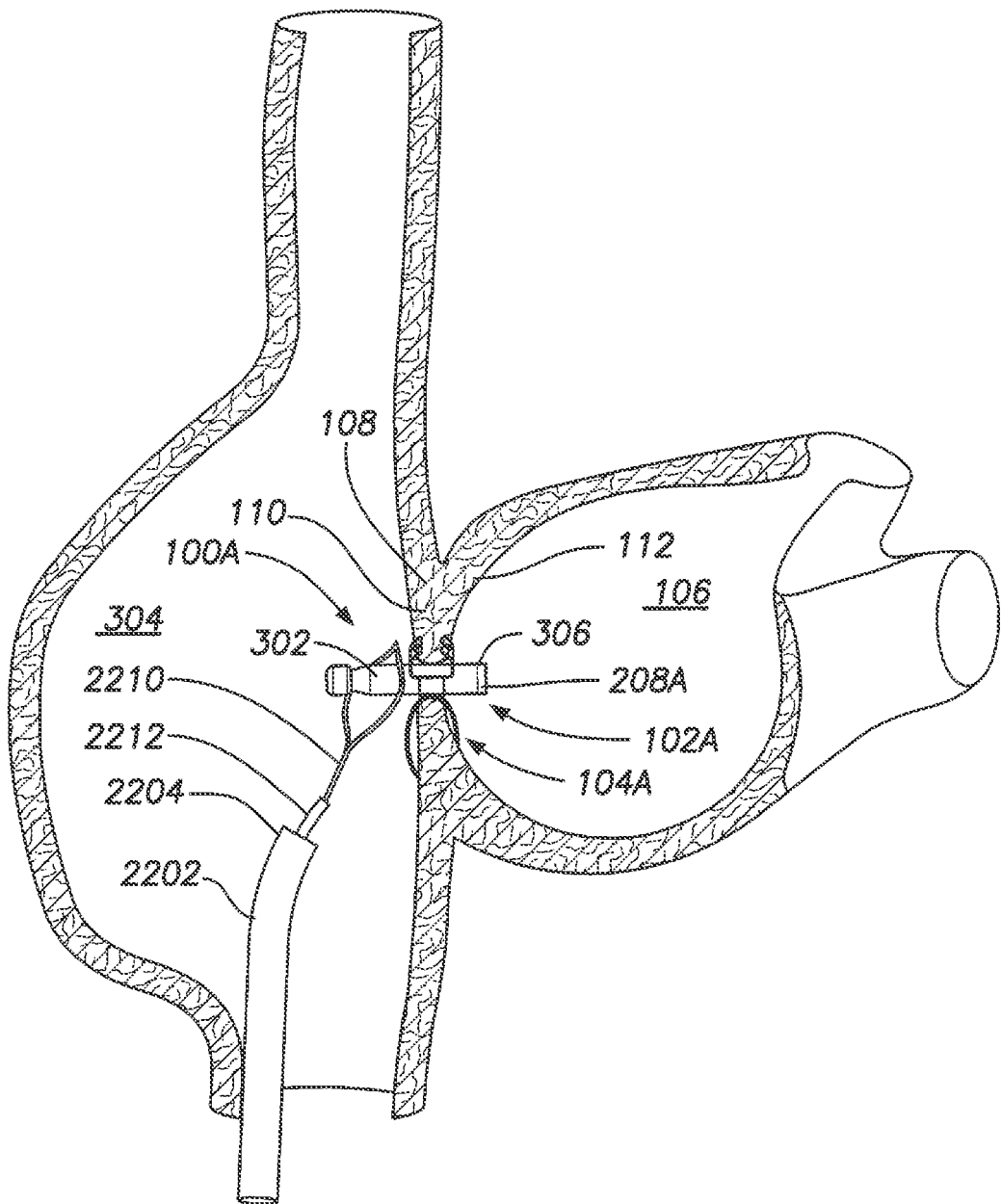

FIGS. 22A-C are cutaway side views of a sheath 2202 containing a wireless LAP sensor device 100 of the embodiment of FIG. 2. Initially the device 100 is in a folded configuration (FIG. 22A) that is progressively advanced at step 2012 of the delivery method 2000 until the device 100 exits the sheath 2202 (FIG. 22B) and the anchors 104 are allowed to fully expand (FIG. 22C) once the device 102 extends through the heart wall (FIG. 22D). In this aspect, the wireless LAP sensor device 100 is similar to the device 100 illustrated in FIG. 2. As shown in FIG. 22A, the sensor 102 is situated near the distal end 2204 of the sheath 2202 and the anchoring elements 104 in the folded configuration extend in a proximal direction 2206 toward a guide tube 2208. The free ends of the anchoring elements 104 may be attached to one or more tethers 2210 protruding from the distal end 2212 of the guide tube 2208. The sheath 2204 maintains the device 100 in a folded configuration during the situation of the sensor 102 within the left atrium of the patient. In addition, as shown in FIG. 22B, the sheath may be made to slide in a proximal and/or distal direction to expose at least a portion of the device 100 during implantation. As the sheath 2202 is slid in a proximal direction 2206 to expose portions of the device, those parts of the device that are constructed of elastic elements, such as the anchoring elements 104, may elastically rebound to revert to the unfolded configuration suitable for anchoring the device 100, as illustrated in FIG. 22C to be implanted or anchored in the heart wall as shown in FIG. 22D.

In one aspect, the one or more tethers 2210 may control the position of the sensor 102 and anchoring elements 104 during implantation. In addition, the one or more tethers may be reattached to the anchoring elements, sensor housing, or any other suitable snagging structure incorporated into the device 100 in order to retrieve the device 100 if necessary.

The remaining steps of the method 2000 may differ depending on the design of the device 100 to be implanted.

a. Implanting Rectangular/Prismatic Sensor

To accomplish the anchoring of a device 100 that includes a sensor 102 with a rectangular or prismatic profile, similar to the devices illustrated in FIGS. 1-2, the remaining steps of the method 2000 entail positioning the sensor 102 adjacent to the left wall of the atrial septum and the anchoring elements 104 adjacent to the right wall of the atrial septum.

Referring back to FIG. 20, the catheter and sheath were advanced into the left atrium at step 2012. As can be understood from FIGS. 22B-D, at step 2014, the catheter and sheath are withdrawn together to situate the sensor against the left wall of the atrial septum within the left atrium and the anchoring bodies within the right atrium; the atrial septum is situated between the sensor and the anchoring elements. At step 2016, the sheath is withdrawn to deploy the anchor elements in the right atrium (FIG. 22D). The tether can be used to adjust the positioning of the device in the heart wall and, once a desired positioning and anchoring arrangement is achieved, the tether can be detached, per step 2018. The catheter and sheath can then be withdrawn from the patient (step 2020).

Figure 23A:
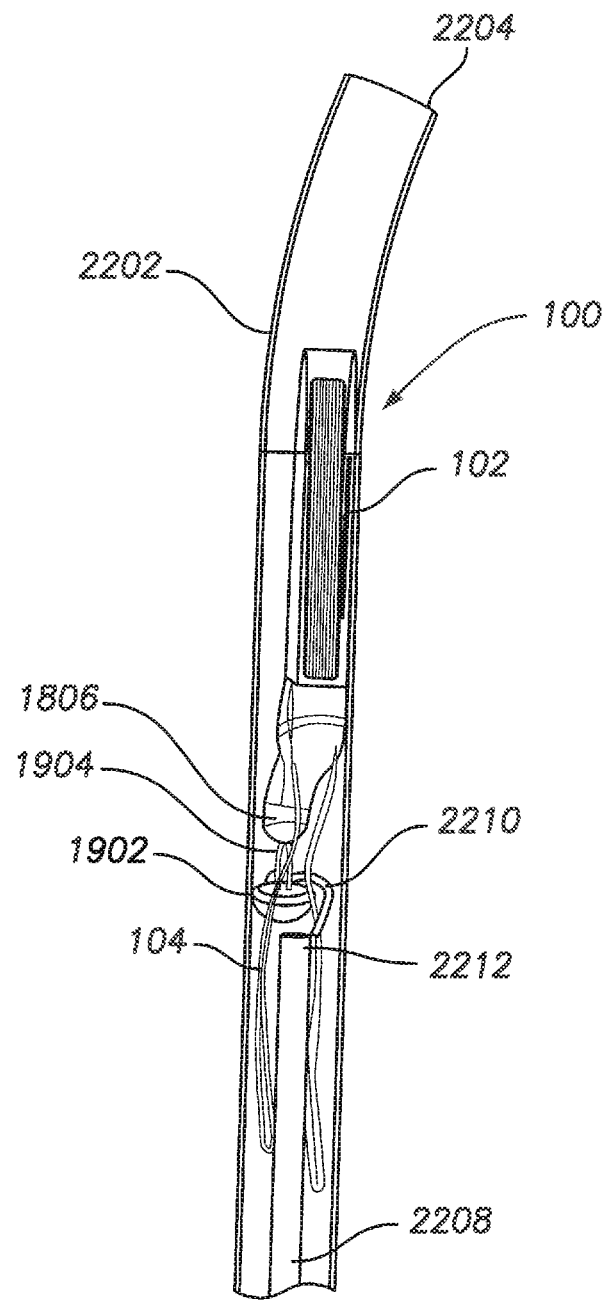
FIGS. 23A-G are various views of a wireless LAP sensor device and a sheath for the delivery thereof, the device being illustrated at various steps in the course of being implanted.
Figure 23B:
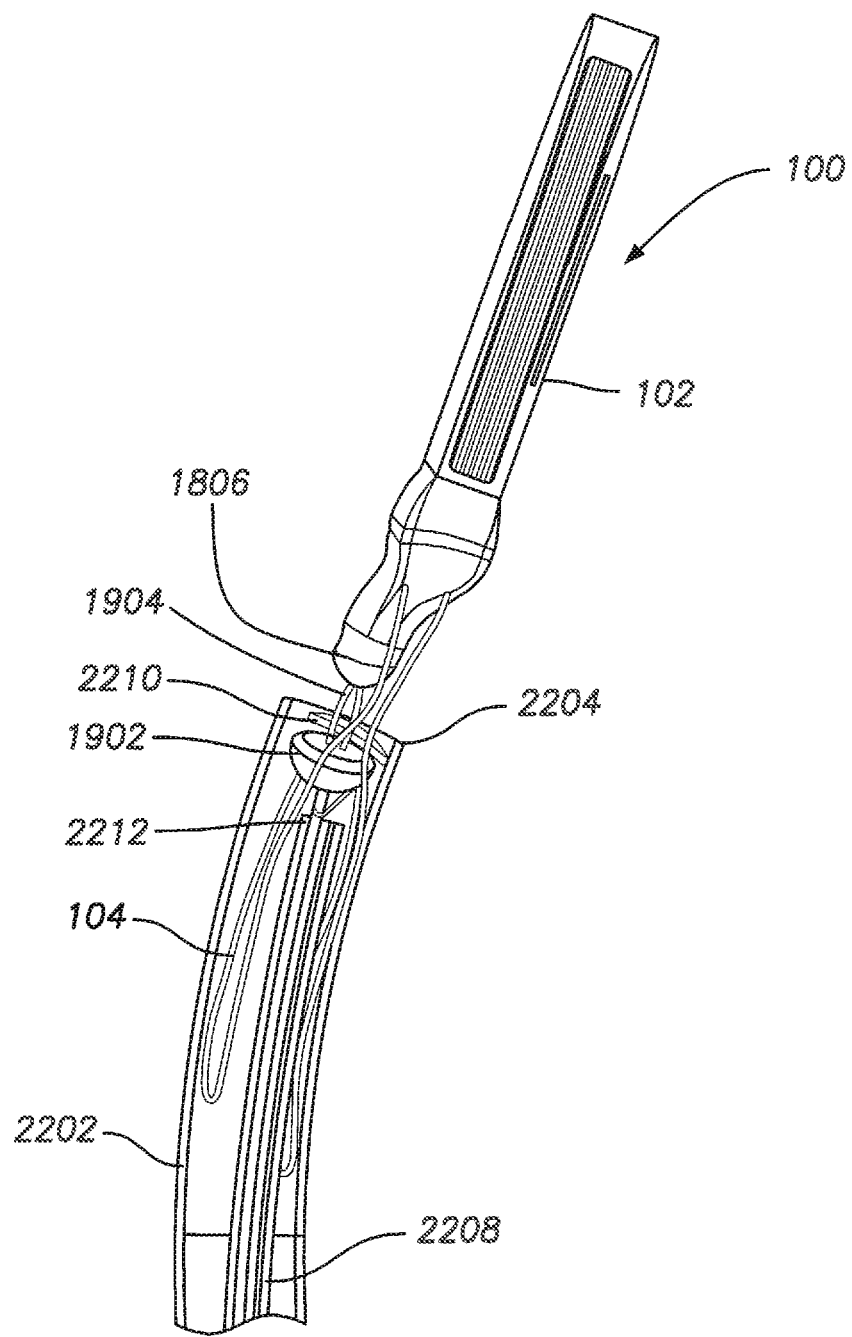
Figure 23C:
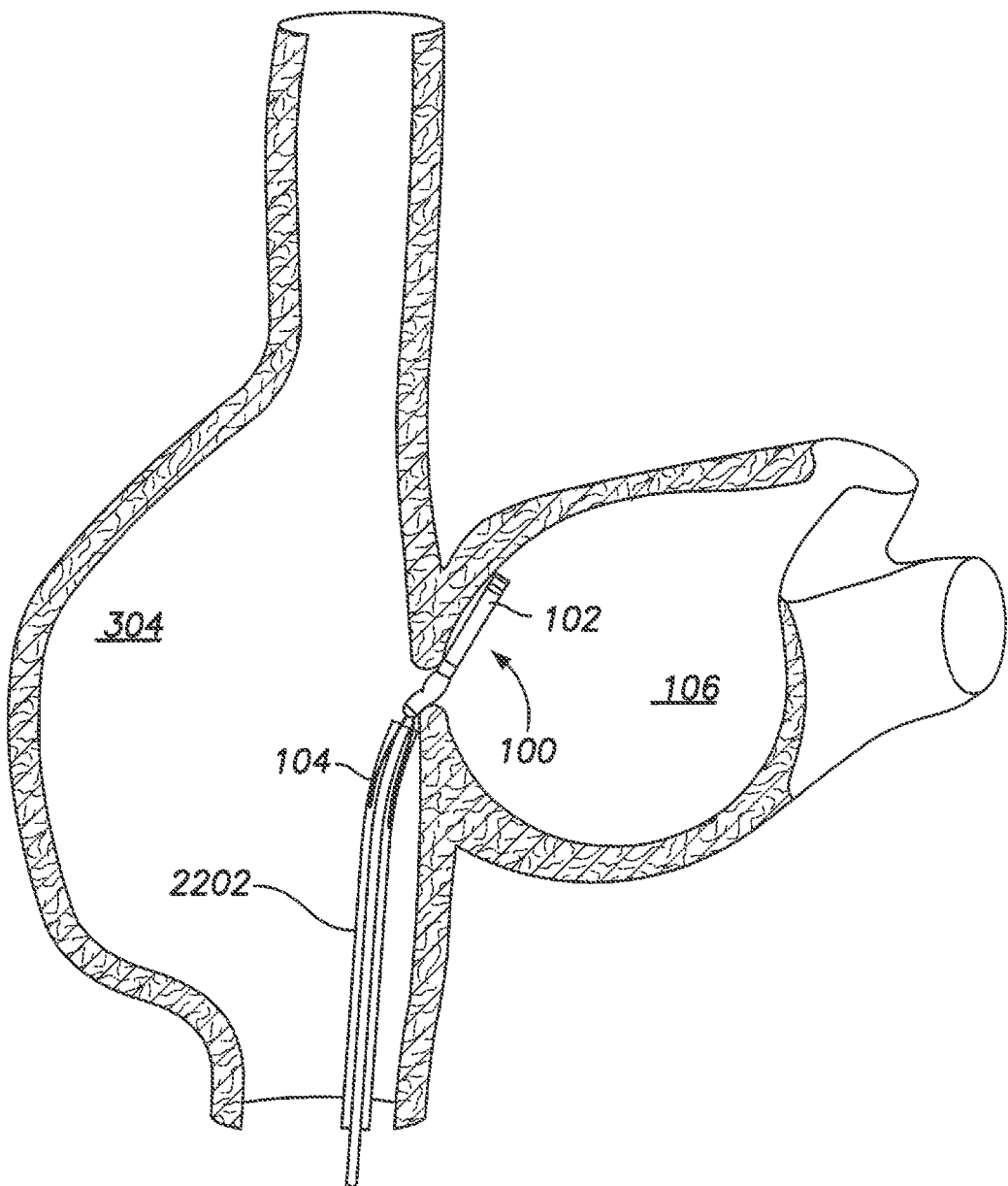

A similar method of implantation may be used for devices 100 that include snaring elements such as the knob 1806 and/or extension plug 1902 as illustrated in FIGS. 18A-19B with minor modifications. For a specific discussion regarding the delivery of the device embodiment of FIGS. 19A-B, reference is made to FIGS. 23A-F, which are cutaway side views of a sheath 2202 containing a wireless LAP sensor device 100 being progressively deployed. A tether snare loop 2210 is attached to the extension plug 1902 of the device at step 2022. The device is initially in a folded configuration (FIG. 23A) that is progressively advanced at step 2024 of the delivery method 2000 until the device 100 exits the sheath 2202 (FIG. 23B) and is extended through the heart wall (FIG. 23C). As can be understood from FIG. 23C, although the device extends through the heart wall, the anchoring elements 104 remain encased inside of the sheath 2202 at the completion of step 2024, thereby maintaining the anchoring elements 104 in a folded position.

Figure 23D:
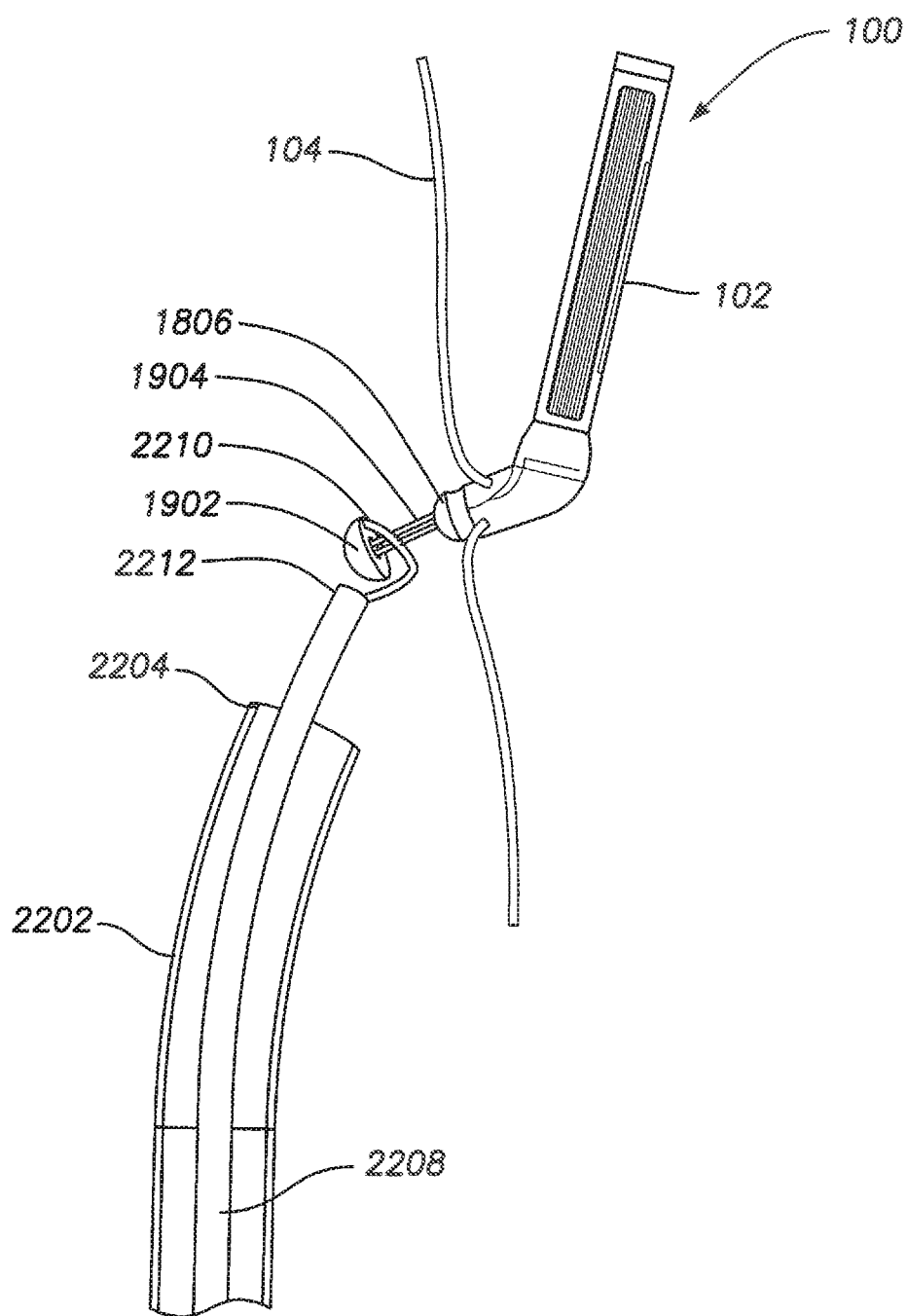
Figure 23E:
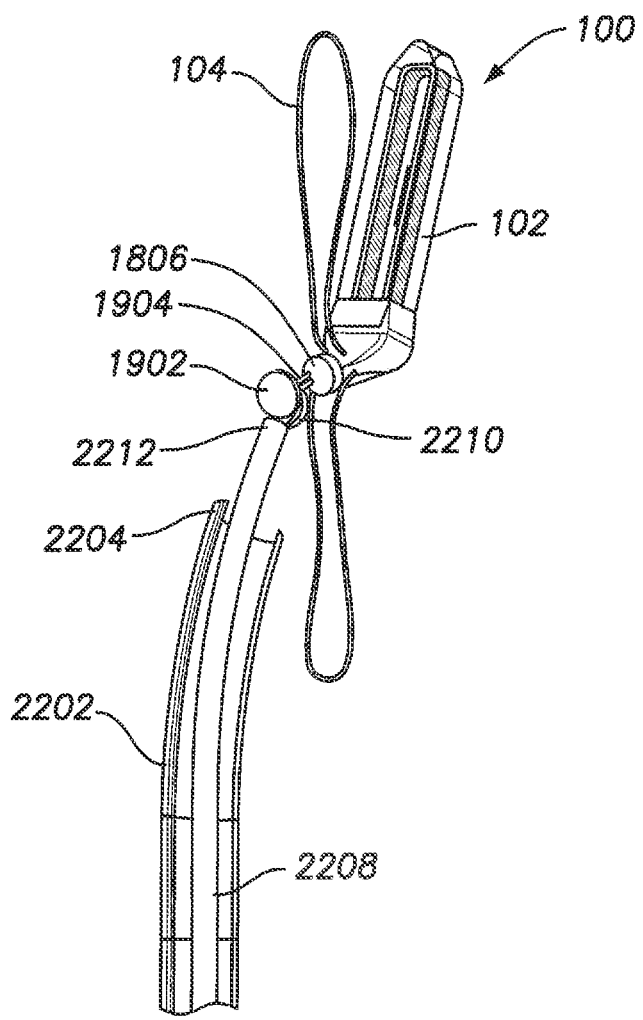
Figure 23F:
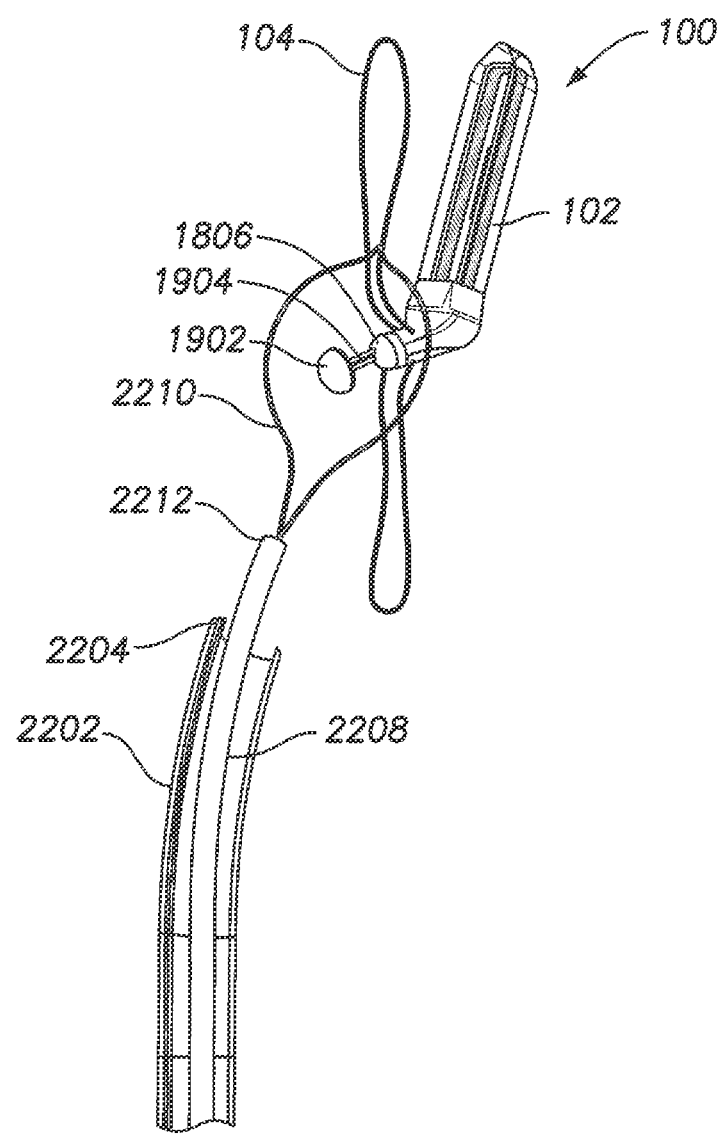
Figure 23G:
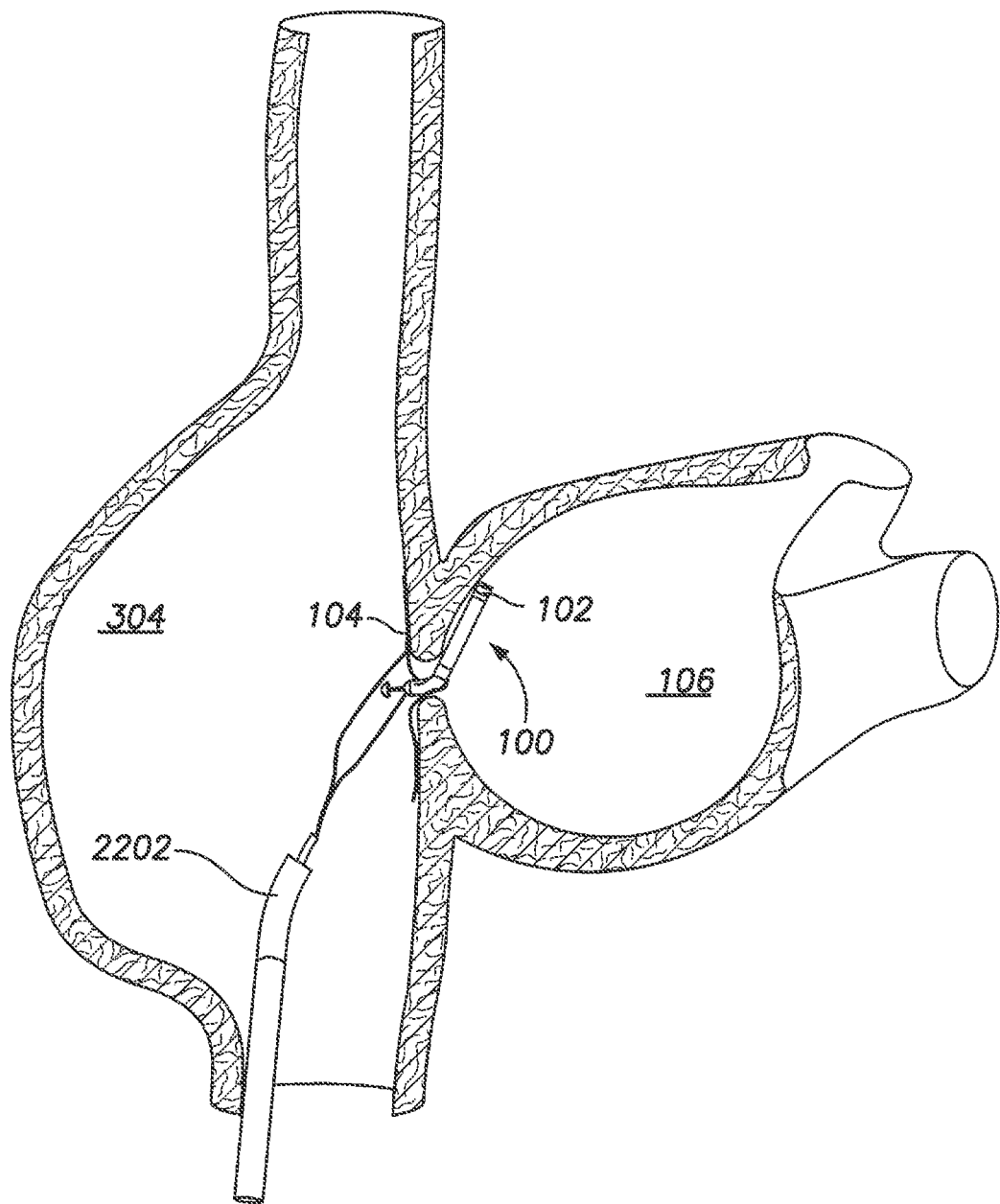

Once the device extends through the heart wall, the anchors 104 are then allowed to fully expand (FIG. 23D-E). Specifically, the sheath is withdrawn to deploy the anchoring elements at step 2026. After the completion of step 2026, the anchors 104 and device 102 act on the heart wall (FIGS. 23F-G) to anchor the device in place. The sensor 102 is now situated in the left atrium 106 and the anchoring elements 104 are situated in the right atrium 304. The tether 2210 remains attached to the extension plug 1902 after the completion of step 2026 to provide a means of adjusting the position of the device 100 and/or removing the device 100 if needed.

After confirming proper placement of the sensor and anchoring elements, and/or performing any final adjustments to the positions of the sensor and/or anchoring elements, the tether is detached from the extension plug 1902 at step 2030. Specifically, the tether may then be detached by operating a mechanism at the proximal end of the snare catheter at step 2030. If the sensor was deployed incorrectly, the tether can be used to pull the sensor back into the sheath and then redeployed in the correct position. The catheters and sheath may then be withdrawn from circulation at step 2032 to complete the implantation of the device.

The method of implantation discussed above with respect to the embodiment of FIGS. 19A-B and FIGS. 23A-G may be used for the device 100 that includes a snaring element in the form of a knob 1806 with minor modifications.

b. Implanting Cylindrical Sensor

Figure 24:
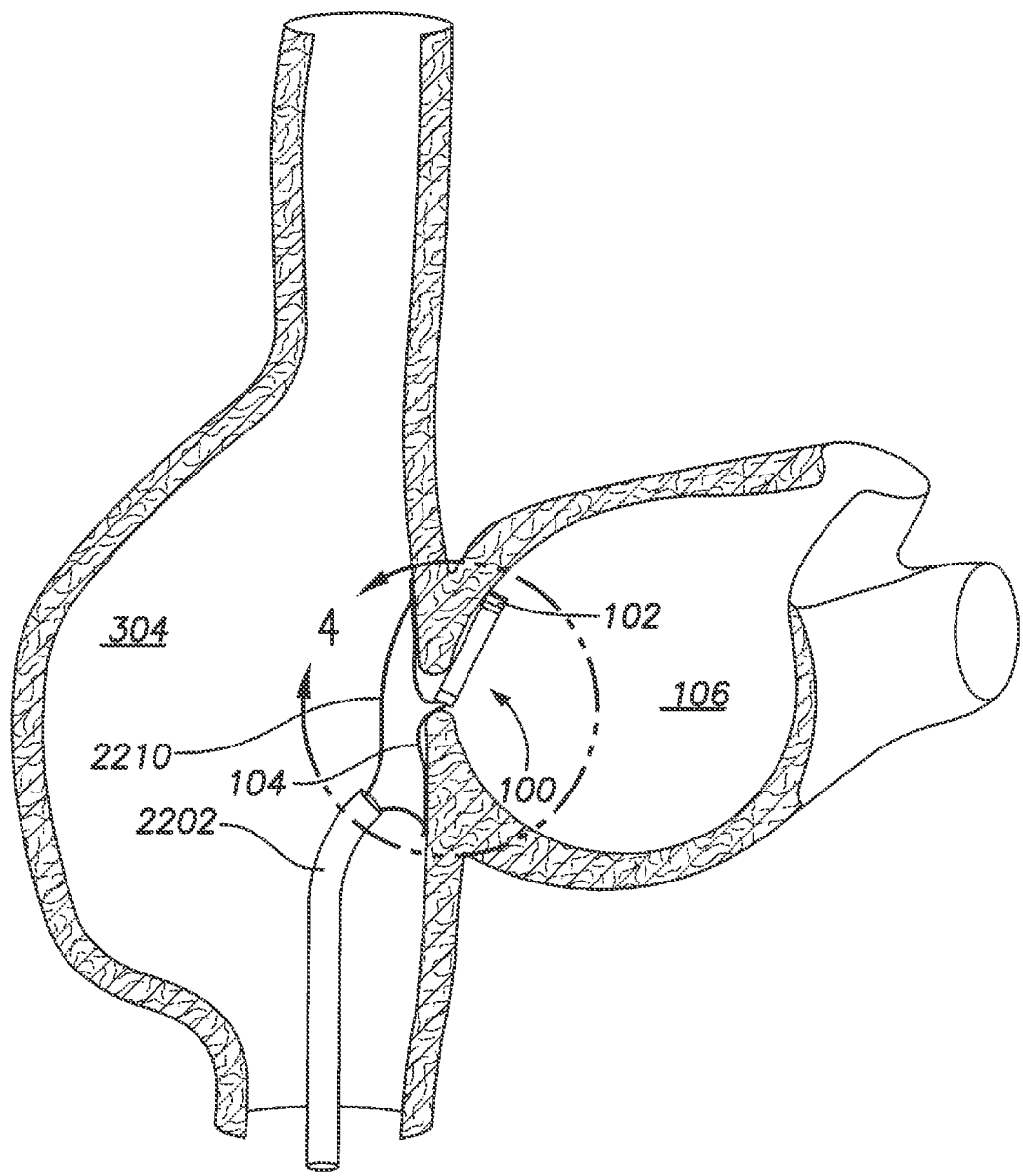
FIG. 24 is a side view of a wireless LAP sensor device situated within the left atrium in which the device is anchored in place, but still attached to the tethers.

To implant a device 100 that includes both proximal and distal anchoring elements 104, such as the cylindrical sensor illustrated in FIG. 3, a modified method 2000 may be used. The device 100, which is attached to the tether within the sheath, may be advanced through sheath until the distal anchoring elements are deployed at step 2034. The sensor and sheath are then withdrawn together until the distal anchor elements are flush with septum wall in the left atrium at step 2036. The sheath only is then withdrawn until the proximal anchoring elements are deployed against the septum wall in right atrium at step 2038. As illustrated in FIG. 24, the tether may then be detached at step 2040 and the catheters and sheath may then be withdrawn from circulation at step 2042 to complete the implantation of the device.

c. Method of Extracting Sensor

In various aspects, the device 100 may be extracted from the patient using a procedure that is essentially the reverse of the deployment method 2000 illustrated in FIG. 20. A catheter-based snare may be used to grab the extension plug 1902, knob 1808, or other snagging structure incorporated into the device 100. Once the device 100 is snagged, the device 100 may be withdrawn from the atrial septum by applying traction to the extension plug 1902, knob 1808 or other snagging structure via the snare. An outer sheath provided with the catheter may be used to provide countertraction and to facilitate the deformation of the anchoring elements 104 into the folded configuration within the sheath, allowing for the safe extraction of the device 100.

The foregoing merely illustrates the principles of the technology disclosed herein. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosed technology and are thus within the spirit and scope of the disclosed technology. From the above description and drawings, it will be understood by those of ordinary skill in the art that the particular embodiments shown and described are for purposes of illustrations only and are not intended to limit the scope of the disclosed technology. References to details of particular embodiments are not intended to limit the scope of the disclosed technology.

What is claimed is:

1. An implantable pressure measurement device comprising:
   a wireless pressure sensor;
   a first anchoring element coupled to the wireless pressure sensor, wherein the first anchoring element has a flattened lobe profile that extends a length from a fixed end of the first anchoring element at the wireless pressure sensor to a free end of the first anchoring element, the free end being rounded; and
   a second anchoring element coupled to the wireless pressure sensor, wherein the first anchoring element is configured to press against a first wall of an atrial septum of a patient and at least one of the second anchoring element or a surface of the wireless pressure sensor is configured to press against a second wall of the atrial septum to secure the wireless pressure sensor in place within a left atrium of the patient, wherein the first anchoring element has a curvature along the length to impart a spring force against the first wall of the atrial septum, wherein the first wall of the atrial septum extends along a right atrium of the patient and the second wall of the atrial septum extends along the left atrium.

2. The implantable pressure measurement device of claim 1, wherein the first anchoring element is a wire frame having a composition that includes a shape memory nickel titanium alloy.

3. The implantable pressure measurement device of claim 1, wherein the first anchoring element includes a wire frame and an elastic web attached to the wire frame, the elastic web configured to contribute to a contact surface area between the first anchoring element and the first wall of the atrial septum.

4. The implantable pressure measurement device of claim 1, wherein the first anchoring element comprises a solid sheet of a resilient material.

5. The implantable pressure measurement device of claim 4, wherein the first anchoring element is curved about a longitudinal axis of the first anchoring element, the longitudinal axis extending from the fixed end to the free end.

6. The implantable pressure measurement device of claim 1, wherein the first anchoring element is one of multiple first anchoring elements within a first set coupled to the wireless pressure sensor, and the second anchoring element is one of multiple second anchoring elements within a second set coupled to the wireless pressure sensor, wherein the second set is configured to contact the second wall of the atrial septum.

7. The implantable pressure measurement device of claim 6, wherein the first anchoring elements in the first set are circumferentially spaced apart from one another.

8. The implantable pressure measurement device of claim 1, further comprising a disc through which the first and second anchoring elements extend, the disc configured to contact the first wall of the atrial septum.

9. The implantable pressure measurement device of claim 1, wherein at least one of the first anchoring element or the second anchoring element includes one or more radiopaque marker materials for monitoring a position of the at least one of the first anchoring element or the second anchoring element within the patient.

10. The implantable pressure measurement device of claim 1, wherein each of the first anchoring element and the second anchoring element includes a hydrophilic coating.

11. The implantable pressure measurement device of claim 1, wherein the fixed end of the first anchoring element and a fixed end of the second anchoring element are coupled to a proximal end of the wireless pressure sensor, the first and second anchoring elements biased to project in opposite directions and to both contact the first wall of the atrial septum.

12. An implantable pressure measurement device comprising:
    a wireless pressure sensor;
    a first anchoring element coupled to a proximal end of the wireless pressure sensor, the first anchoring element extending a length from a fixed end of the first anchoring element at the wireless pressure sensor to a free end of the first anchoring element that is rounded; and
    a second anchoring element coupled to the proximal end of the wireless pressure sensor, the second anchoring element extending a length from a fixed end of the second anchoring element at the wireless pressure sensor to a free end of the second anchoring element that is rounded,
    wherein the first and second anchoring element are biased to project in opposite directions from one another and to both press against a first wall of an atrial septum of a patient, wherein at least one of a third anchoring element or a surface of the wireless pressure sensor is configured to press against a second wall of the atrial septum to secure the wireless pressure sensor in place within a left atrium of the patient, wherein each of the first and second anchoring elements has a curvature along the respective length to impart a spring force against the first wall of the atrial septum, wherein the first wall of the atrial septum extends along a right atrium of the patient and the second wall of the atrial septum extends along the left atrium.

13. The implantable pressure measurement device of claim 12, wherein each of the first anchoring element and the second anchoring element is a wire frame having a composition that includes a shape memory nickel titanium alloy.

14. The implantable pressure measurement device of claim 12, wherein each of the first anchoring element and the second anchoring element includes a wire frame and an elastic web attached to the wire frame, the elastic web configured to contribute to a contact surface area between the at least one of the first anchoring element or the second anchoring element and the first wall of the atrial septum.

15. The implantable pressure measurement device of claim 12, wherein each of the first anchoring element and the second anchoring element comprises a solid sheet of a resilient material.

16. The implantable pressure measurement device of claim 15, wherein the first anchoring element is curved about a longitudinal axis of the first anchoring element, the longitudinal axis extending from the fixed end to the free end.

17. The implantable pressure measurement device of claim 12, further comprising a disc through which the first and second anchoring elements extend, the disc configured to contact the first wall of the atrial septum.

18. The implantable pressure measurement device of claim 12, wherein at least one of the first anchoring element or the second anchoring element includes one or more radiopaque marker materials for monitoring a position of the at least one of the first anchoring element or the second anchoring element within the patient.

19. An implantable pressure measurement device comprising:
    a wireless pressure sensor;
    a first anchoring element coupled to the wireless pressure sensor, wherein the first anchoring element has a flattened lobe profile that extends a length from a fixed end of the first anchoring element at the wireless pressure sensor to a free end of the first anchoring element, the free end being rounded;
    a second anchoring element coupled to the proximal end of the wireless pressure sensor, the second anchoring element extending a length from a fixed end of the second anchoring element at the wireless pressure sensor to a free end of the second anchoring element that is rounded; and
    a disc, wherein the first anchoring element and the second anchoring element are configured to extend through the disc, wherein the first anchoring element, the second anchoring element, and the disc are configured to contact a first wall of an atrial septum of a patient and at least one of a third anchoring element or a surface of the wireless pressure sensor is configured to press against a second wall of the atrial septum to secure the wireless pressure sensor in place within a left atrium of the patient, wherein the first wall of the atrial septum extends along a right atrium of the patient and the second wall of the atrial septum extends along the left atrium.

20. The implantable pressure measurement device of claim 19, wherein each of the first and second anchoring elements has a curvature along the respective length to impart a spring force against the first wall of the atrial septum.

* * * * *